United States Patent
Son et al.

(10) Patent No.: US 11,708,596 B2
(45) Date of Patent: *Jul. 25, 2023

(54) ANALYZING AND USING MOTILITY KINEMATICS OF MICROORGANISMS

(71) Applicant: PhAST Corp., Boston, MA (US)

(72) Inventors: Kwangmin Son, Cambridge, MA (US); Roman Stocker, Boston, MA (US)

(73) Assignee: PHAST CORP., Boston, MA (US)

( * ) Notice: Subject to any disclaimer, the term of this patent is extended or adjusted under 35 U.S.C. 154(b) by 1118 days.

This patent is subject to a terminal disclaimer.

(21) Appl. No.: 16/292,608

(22) Filed: Mar. 5, 2019

(65) Prior Publication Data

US 2019/0241928 A1 Aug. 8, 2019

Related U.S. Application Data

(63) Continuation of application No. 15/883,485, filed on Jan. 30, 2018, now Pat. No. 10,266,867.

(60) Provisional application No. 62/453,605, filed on Feb. 2, 2017.

(51) Int. Cl.
| | |
|---|---|
| *C12Q 1/04* | (2006.01) |
| *G02B 21/00* | (2006.01) |
| *G02B 21/36* | (2006.01) |
| *C40B 30/06* | (2006.01) |
| *C40B 40/02* | (2006.01) |
| *G01N 33/94* | (2006.01) |
| *G16C 10/00* | (2019.01) |

(52) U.S. Cl.
CPC ............ *C12Q 1/04* (2013.01); *C40B 30/06* (2013.01); *C40B 40/02* (2013.01); *G01N 33/9446* (2013.01); *G02B 21/0084* (2013.01); *G02B 21/365* (2013.01); *G16C 10/00* (2019.02)

(58) Field of Classification Search
None
See application file for complete search history.

(56) References Cited

U.S. PATENT DOCUMENTS

| | | | |
|---|---|---|---|
| 4,603,977 | A | 8/1986 | Bennett et al. |
| 4,780,907 | A | 10/1988 | Speiser et al. |
| 4,896,966 | A | 1/1990 | Boisseau et al. |
| 5,312,731 | A | 5/1994 | Engstrom |
| 6,251,624 | B1 | 6/2001 | Matsumura |
| 8,460,887 | B2 | 6/2013 | Goldberg et al. |
| 8,497,089 | B2 | 7/2013 | Compagnone |
| 9,522,396 | B2 | 12/2016 | Bachelet et al. |
| 9,677,109 | B2 | 6/2017 | Shamsheyeva et al. |
| 9,851,345 | B1 | 12/2017 | Arab et al. |
| 9,926,526 | B2 | 3/2018 | Newman |
| 10,266,867 | B2 | 4/2019 | Son |
| 10,947,576 | B2 | 3/2021 | Tao et al. |
| 11,079,719 | B2 | 8/2021 | Gusyatin |
| 11,085,064 | B2 | 8/2021 | Ashby et al. |
| 2007/0298454 | A1 | 12/2007 | Green et al. |
| 2008/0286822 | A1 | 11/2008 | Gallager |
| 2012/0003661 | A1 | 1/2012 | Eckert |
| 2013/0315466 | A1 | 11/2013 | Drell |
| 2015/0064703 | A1 | 3/2015 | Super |
| 2015/0160214 | A1 | 6/2015 | Auton |
| 2015/0167045 | A1 | 6/2015 | Brubacher |
| 2015/0317795 | A1 | 11/2015 | Akoulitchev et al. |
| 2016/0102334 | A1 | 4/2016 | Yong-Gyun et al. |
| 2016/0186231 | A1 | 6/2016 | Kreuger |
| 2016/0289729 | A1 | 10/2016 | Richards et al. |
| 2017/0010253 | A1 | 1/2017 | Takahashi et al. |
| 2017/0045514 | A1 | 2/2017 | Tao |
| 2018/0051311 | A1 | 2/2018 | Ekinci |
| 2018/0216155 | A1 | 8/2018 | Son |
| 2019/0241929 | A1 | 8/2019 | Son |
| 2021/0053065 | A1 | 2/2021 | Arab et al. |

FOREIGN PATENT DOCUMENTS

| | | |
|---|---|---|
| JP | 2001161393 | 6/2001 |
| KR | 10-0837349 | 6/2006 |
| WO | WO 2003-012726 | 2/2003 |
| WO | WO2016/166847 | 10/2016 |
| WO | WO 2018027107 | 2/2018 |
| WO | WO 2018/144431 | 8/2018 |

OTHER PUBLICATIONS

Soutourina et al. (Applied and Environmental Microbiology (2001) vol. 67, No. 9:3852-3859.*
Transaction history and application including pending claims of U.S. Appl. No. 62/453,605.
Baltekin, Ozden, et al., "Antibiotic susceptibility testing in less than 30 min using direct single-cell imaging", PNAS Early Edition, www.pnas.org, pp. 1-6, May 23, 2017 (6 pages).
Cheong, Fook Chiong, et al., "Rapid, High-Throughput Tracking of Bacterial Motility in 3D via Phase-Contract Holographic Video Microscopy", Biophysical Journal, vol. 108, pp. 1248-1256, Mar. 2015 (9 pages).
Choi, Jungil, et al., "A Rapid antimicrobial susceptibility test based on single-cell morphological analysis", www.SciesceTranslationalMedicine.org, vol. 6, Issue 267, Dec. 17, 2014 (36 pages).
David, Russel O. et al., "Quantitative analysis of sperm motion kinematics from real-time videoedge images", Division of reproductive Biology and Medicine, School of Medicine, University of California, Davis, CA 95616, SPIE vol. 832, High Speed Photography, Videography, and Photonics V, 1987 (7 pages).
De Jong, Imke G., "Live Cell Imaging of Bacillus subtilis and Streptococcus pneumoniae using Automated Time-Lapse Microscopy", http://www.jove.com/video/3145, doi:10.3791/3145, Jul. 28, 2011 (6 pages).

(Continued)

*Primary Examiner* — Lori A. Clow
(74) *Attorney, Agent, or Firm* — Pearl Cohen Zedek Latzer Baratz LLP

(57) ABSTRACT

Among other things, motility of at least one individual microorganism or a change in motility of at least one individual microorganism or both is or are characterized. The characterized motility or change in motility is used to detect the presence or count of the at least one individual microorganism, or determine the identity of a species or strain of the at least one individual microorganism, or determine a susceptibility of the at least one individual microorganism to one or more antibiotics or other antimicrobials.

25 Claims, 21 Drawing Sheets

(56) References Cited

OTHER PUBLICATIONS

Figure 1:
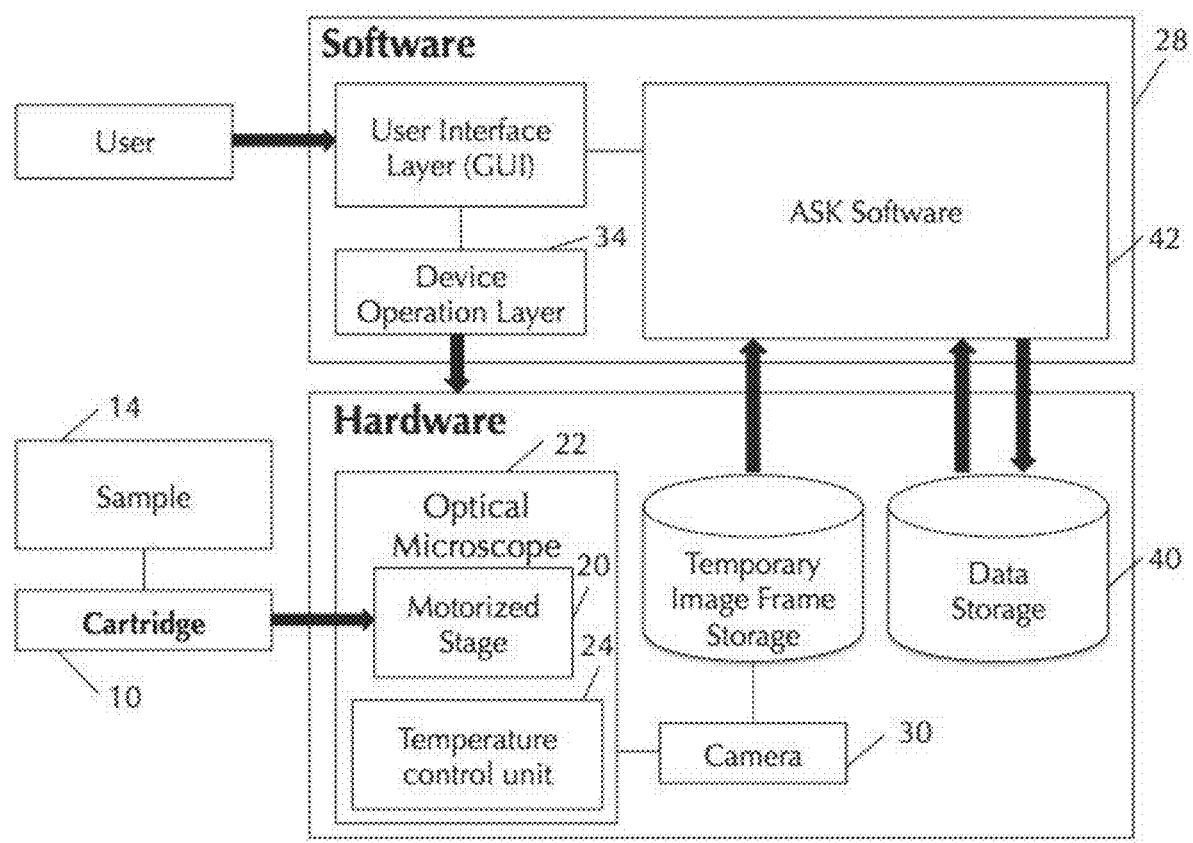

Emonet, Thierry, et al., "AgentCell: a digital single-cell assay for bacterial chemotaxis", The Institute for Biology Dynamics and the James Franck Institute, The University of Chicago, Bioformatics, vol. 21, No. 11, pp. 2714-2721, doi:10.1093/bioinfomiatics/bti391, 2005 (8 pages).

Fonseca, A.P., et al., "Effect of antibiotic-induced morphological changes on surface properties, motility and adhesion of nosocomial Pseudomonas aeruginosa strains under different physiological states", Department of Microbiology, Journal of Applied Microbiology, ISSN 13644-5072, 2006 (10 pages).

Graff, Jason R., et al. "Vibrio cholera Exploits Sub-Lethal Concentrations of a Competitor-Produced Antibiotic to Avoid Toxic Interactions", The University of Rhode Island Graduate School of Oceanography, 2013 (12 pages).

Hoffman, Lucas R., et al. "Aminoglycoside antibiotics induce bacterial biofilm formation", Nature, vol. 436, No. 25, Aug. 2005, doi: 10,1038/nature03912 (5 pages).

Hol, Felix JH., et al., "Density-dependent adaptive resistance allows swimming bacteria to colonize an antibiotic gradient", The ISME Journal, www.nature.com/ismej, 2016 (9 pages).

Hu, Wei, et al., "Interplay between type IV pili activity and exopolysaccharides secretion controls motility patterns in single cells of myxococcus xanthus", Scientific Reports, www.nature.com/scientificreports, 6:17790, doi:10.1038/srep17790, Jan. 19, 2016 (10 pages).

Jorgensen, James H et al., "Antimicrobial Susceptibility Testing: A Review of General Principles and Contemporary Practices", Medical Microbiology, CID 2009:49, Dec. 1, 2009 (7 pages).

King, Kelly, et al., "Antibiotics: effect on cryopreserved-thawed human sperm motility in vitro", Fertility and Sterility, vol. 67, No. 6, American Society for Reproductive Medicine, Jun. 1997 (6 pages).

Lauga, Erica, "Bacterial Hydrodynamics", Annual Review Fluid Mechanic 2016-48:105-130, www.annualreviews.org, 2016 (28 pages).

Lauga, Erica et al., "The hydrodynamics of swimming microorganisms", Reproductive Program Phys., Dec. 15, 2008 (58 pages).

Linares, J.F et al., "Antibiotics as intermicrobial signaling agents of weapons", PNAS, www.pnas.org, Dec. 19, 2006 (6 pages).

MS100-S25, "Performance Standards for Antimicrobial Susceptibility Testing; Twenty-Fifth Informational Supplement", Jan. 2015 (240 pages).

Matsumoto, Yoshimi et al., "A Microfluidic Channel Method for Rapid Drug-Susceptibility Testing of Pseudomonas aeruginosa", PLOS ONE: DOI: 10.1371/journal.pone.0148797, Feb. 12, 2016 (17 pages).

Ritchie, Ken, et al., "Single-molecule imaging in live bacteria cells", Philosophical Transactions of the Royal Society, Department of Physics, Purdue University, 2012, pp. 1-8.

Schoepp, Nathan G., et al., "Rapid pathogen-specific phenotypic antibiotic susceptibility testing using digital LAMP quantification in clinical samples", Science Translational Medicine, Research Article, Antibiotic Resistance, 2017 (13 pages).

Wang, Ping, et al., "Robust Growth of *Escherichia coli*" NIH Public Access Author Manuscript, Curr. Biol. 20; 20(12): 1099-1103, Jun. 22, 2010 (10 pages).

Wiegand, Irith, et al., "Agar and broth dilution methods to determine the minimal inhibitory concentration (MIC) of antimicrobial substances", Protocol, Jan. 17, 2008 (13 pages).

International Search Report and Written Opinion from corresponding PCT application PCT/US2018/015890 dated Apr. 5, 2018 (13 pages).

Son et al. Nature Reviews (2015) vol. 13:761-775.

Son et al. (2016) PNAS vol. 113, No. 31:8624-8629.

Machine Translation to English of JP2001161393 (Jul. 29, 2018); 5 pages.

U.S. Appl. No. 15/883,485, filed Jan. 30, 2018—Issued 2018/0216155 U.S. Pat. No. 10,266,867.

U.S. Appl. No. 16/361,016, filed Mar. 21, 2019—Pending.

Office Action for Japanese Application 2019-563321 dated Sep. 3, 2021.

Office Action for Korean Application 10-2021-7025830 dated Dec. 10, 2021.

USPTO Transaction history for U.S. Appl. No. 15/883,485, Son et al., filed Jan. 30, 2018 (U.S. Pat. No. 10,266,867).

USPTO Transaction history for U.S. Appl. No. 16/361,016, Son et al., filed Mar. 5, 2019.

Extended European Search Report in European Application No. 18747901.9, dated Jan. 30, 2020, 10 pages.

PCT International Preliminary Report on Patentability in International Application No. PCT/US2018/015890, dated Aug. 6, 2019, 9 pages.

U.S. Appl. No. 16/292,608, filed Mar. 5, 2019—Published 20190241928.

U.S. Appl. No. 16/361,016, filed Mar. 21, 2019—Published 20190241929.

* cited by examiner

ANALYZING AND USING MOTILITY KINEMATICS OF MICROORGANISMS

CROSS-REFERENCE To RELATED APPLICATIONS

This application is a continuation application of and claims priority under 35 U.S.C. § 120 to U.S. patent application Ser. No. 15/883,485, filed on Jan. 30, 2018, which is entitled to the benefit of the priority of the filing date of U.S. patent application Ser. 62/453,605, filed on Feb. 2, 2017. Each application is incorporated in its entirety by reference.

BACKGROUND

This description relates to analyzing and using motility kinematics of microorganisms.

Motility kinematics have been analyzed and used, for example, in the context of sperm studies. For example, Green (US patent publication 2007/0298454) described tracking spermatozoa in a sample and deriving properties of motility (such as velocity and trajectory) with the goal of determining whether spermatozoa exhibit normal morphology and motility.

King et al. (*Antibiotics: Effect on cryopreserved-thawed human sperm motility in vitro*, Fertility and Sterility, 1997, vol. 67, no. 6, pp. 1146-1151) used a commercial system to analyze motility of spermatozoa incubated over a 48-hour period in the presence of antibiotics to assess their fertilizing capacity.

Detecting bacterial presence and counts, identification (ID), and antibiotic susceptibility testing (AST) are used to determine the best treatment option for a bacterial infection.

SUMMARY

In general, in an aspect, motility of at least one individual microorganism or a change in motility of at least one individual microorganism or both is or are characterized. The characterized motility or change in motility is used to detect the presence or count of the at least one individual microorganism, or to determine the identity of a species or strain of the at least one individual microorganism, or to determine a susceptibility of the at least one individual microorganism to one or more antibiotics or other antimicrobials.

Implementations may include one or a combination of two or more of the following features. The imaging device is used to capture at successive times two or more digital images of the at least one individual microorganism. The images are processed by computer to determine trajectory data for the at least one individual microorganism. The motility kinematics data are processed by computer for the at least one individual microorganism or a population of the individual microorganisms. The generated motility kinematics data are compared by computer to available motility kinematics data of one or more microorganisms. The motility kinematics data generated by computer are compared to available motility kinematics data of one or more microorganisms to determine the identity of a species or strain of the at least one individual microorganism, or determine a susceptibility of the at least one individual microorganism to the one or more antibiotics or other antimicrobials. The generated motility kinematics data are obtained from digital images captured for a first portion of a sample containing the at least one individual microorganism and the available motility kinematics data of one or more microorganisms comprise motility kinematics data determined from digital images captured from the first portion of the sample at a different time or from a different portion of the sample at the same time or at a different time. The at least one individual microorganism is subjected to two different antibiotic or other antimicrobial conditions, including at least one of: presence and absence of an antibiotic or other antimicrobial, presence of two or more different antibiotics or other antimicrobials, presence of different concentrations of an antibiotic or other antimicrobial, or presence of different combinations of one or more antibiotics or other antimicrobials. The at least one individual microorganism is in a sample that includes one or a combination of two or more of: a bodily sample, a bacterial culture, a fluid, a solid, debris, a non-fluid sample material, ground food, food particles, an environmental sample, a preservative, an anticoagulant, a clot activator, a gel-barrier, a bacterial growth stabilizer, an antiglycolytic agent, or an additive. The statistical significance of the characterized motility or change in motility is determined by computer. The available motility kinematics data of the one or more microorganisms are stored in a motility database that is part of a database management system. The known identity of a species or strain of one or more microorganisms is stored in a database that is part of a database management system. A statistical significance of the characterized motility or change in motility alone or in combination with at least one other characteristic, is determined by computer processing. The at least one other characteristic includes a count, a morphological feature, or a spatial arrangement of two or more microorganisms. The morphological feature includes one or a combination of two or more of the following: shape, aspect ratio, convexity, area, size, dimension, direction of major axis, departure from spherical shape, or distribution of intensity. The spatial arrangement includes a spatial arrangement of a microorganism that is dividing, a spatial arrangement of a cluster of individual microorganisms, positions of two or more microorganisms relative to each other, one or more distances between them, a formation of specific clusters or chains of the microorganisms. The at least one individual microorganism includes one or a combination of two or more of the following: bacterial pathogens, other bacteria, other pathogens, fungi, archaea, protists, plankton, or eukaryotic cells. The at least one individual microorganism is in a sample and is susceptible to one or more antibiotics or other antimicrobials in the sample or is resistant to one or more antibiotics or other antimicrobials in the sample. A computer determines and stores information about a count of individual microorganisms in a sample or a morphological feature of individual microorganisms in a sample or a spatial arrangement of two or more individual microorganisms in a sample. The processing of the images to determine trajectory data for the at least one individual microorganism includes (a) locating microorganisms in images based on at least one of color, pixel intensity gradient, shape, aspect ratio, convexity, area, size threshold, horizontal and vertical location, size, intensity, direction of major axis, departure from spherical shape, or distribution of intensity, and (b) constructing trajectory data by linking the same microorganisms located in the two or more images based on at least one of position, proximity of position, direction, velocity, acceleration, or search radius. The generation of motility kinematics data for the at least one individual microorganism includes determining, by computer, at least one of the following: trajectory, shape of trajectory, speed, acceleration, mean square displacement, swimming direction, rate of turning, angle of turning, temporal sequence of turning angles, diffusivity, net-to-grossdisplacement ratio, curvature, concentration of motile cells, or ratio of motile to non-motile cells. The imaging device is used to capture at successive times one, two, or more digital images of a sample containing the at least one individual microorganism, the sample containing one or more antibiotics or other antimicrobials, and the imaging device is used to capture at a time prior to the successive times one, two, or more digital images of individual microorganisms in the sample, the sample at the prior time containing a different proportion of antimicrobial or the sample at the prior time being free of the antimicrobial. The imaging device is used to capture simultaneously one, two or more digital images of two or more samples containing the at least one individual microorganism, at least one sample of the samples containing one or more antibiotics or other antimicrobials, and the imaging device is used to capture simultaneously one, two or more digital images of two or more samples containing the at least one individual microorganism, at least one sample of the samples containing a different proportion of antibiotic or other antimicrobial or at least one sample of the samples being free of the antibiotic or other antimicrobial. The presence, absence, or count of motile microorganisms is determined in a pre-screening step. At least one environmental condition is changed to stimulate motility of the at least one individual microorganism in order to favor the detection of the microorganism, the identification of a species or strain of the microorganism, or the determination of antimicrobial susceptibility of the microorganism. The non-moving entities are removed from the images by image analysis or from the sample physically prior to imaging. The at least one individual microorganism corresponding to the generated motility kinematics data is subjected to a first antibiotic or other antimicrobial at a first time, and the available motility kinematics data is associated with individual microorganisms subjected to the first antibiotic or antimicrobial at a second time or to a different antibiotic or other antimicrobial at a second time. The at least one individual microorganism corresponding to the generated motility kinematics data includes at least one individual microorganism of a species, and the available motility kinematics data is associated with the species. The portions of a sample containing the at least one individual microorganism are loaded into one or more wells, and none or one or more of the portions of the sample are subjected to an antibiotic or other antimicrobial. The two portions of a sample containing the at least one individual microorganism are loaded into two different wells and are subjected to two different antibiotic or antimicrobial conditions. The susceptibility of the at least one individual microorganism is determined without requiring the identity of the species or strain of the at least one individual microorganism to be determined.

In general, in an aspect, the wells (by which we mean any device that can contain a sample as discussed later) can be part of a cartridge. Implementations may include one or a combination of two or more of the following features. One or more portions of a sample are loaded into one or more wells of the cartridge. One or more antibiotics or other antimicrobials are added to the sample in none, one, or two or more of the wells. Different antibiotics or other antimicrobials can be added to the sample in the same or in different wells. Different concentrations of one ore more antibiotics or other antimicrobials can be added to the sample in the same or in different wells. At least one of the wells protrudes from a base plate. At least one of the wells is indented in the base plate. Each of the wells can have an exposed opening. Each of the wells can have no exposed opening. A cover seals any exposed openings of the wells. Each of the wells or the cover or both are characterized by at least one of the following: untreated surfaces, surfaces treated to be resistant to attachment of microorganisms, or surfaces treated to be supportive of attachment of microorganisms, material that fosters attachment of microorganisms, or material that deters attachment of microorganisms.

The cover includes a solid material. The solid material includes a glass. The solid material includes a plastic. The solid material includes a metal. The cover includes a film. The film includes an adhesive film. The film includes a non-adhesive film. The cover has one or more openings. The cover has no opening. The cover includes a solid material. The cover is flexible. The cover is rigid. The cover is gas permeable. The cover is gas impermeable. The cover is flat. The cover is patterned. The cover includes a membrane. The cover is re-sealable.

These and other aspects, features, implementations, and advantages can be expressed as methods, apparatus, systems, components, program products, business methods, means or steps for performing functions, and in other ways.

These and other aspects, features, implementations, and advantages will become apparent from the following description and from the claims.

DESCRIPTION

Figure 2:
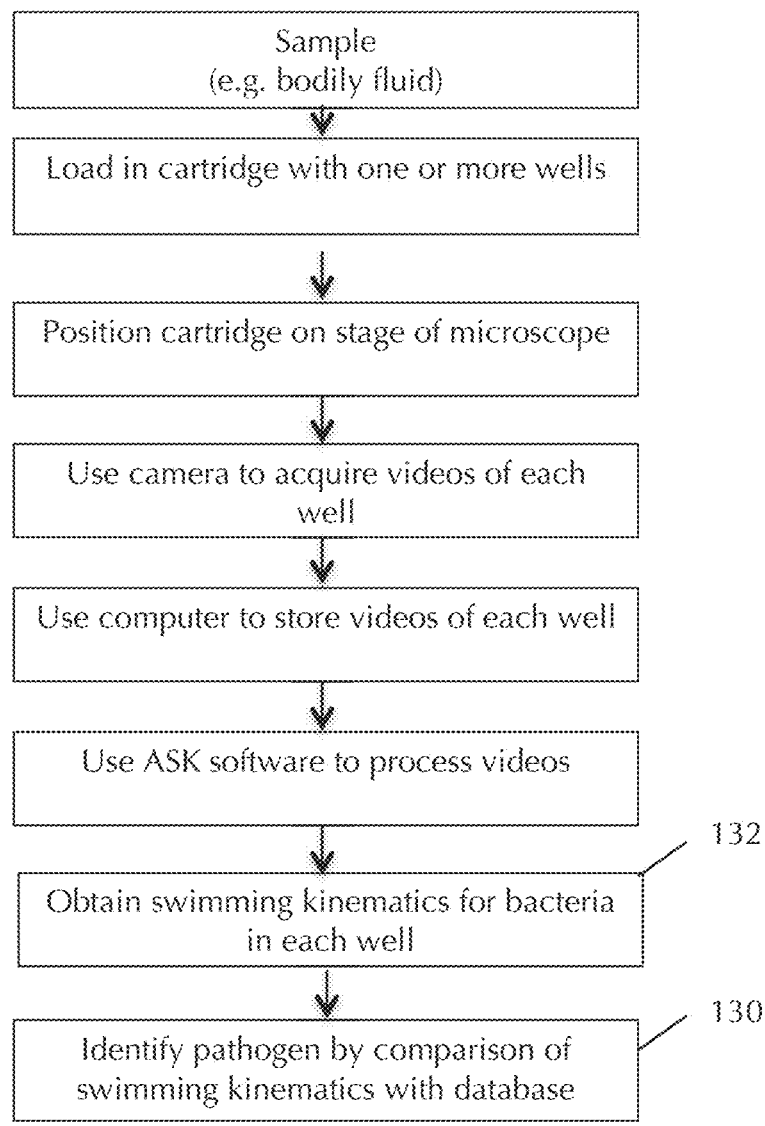
Figure 3:
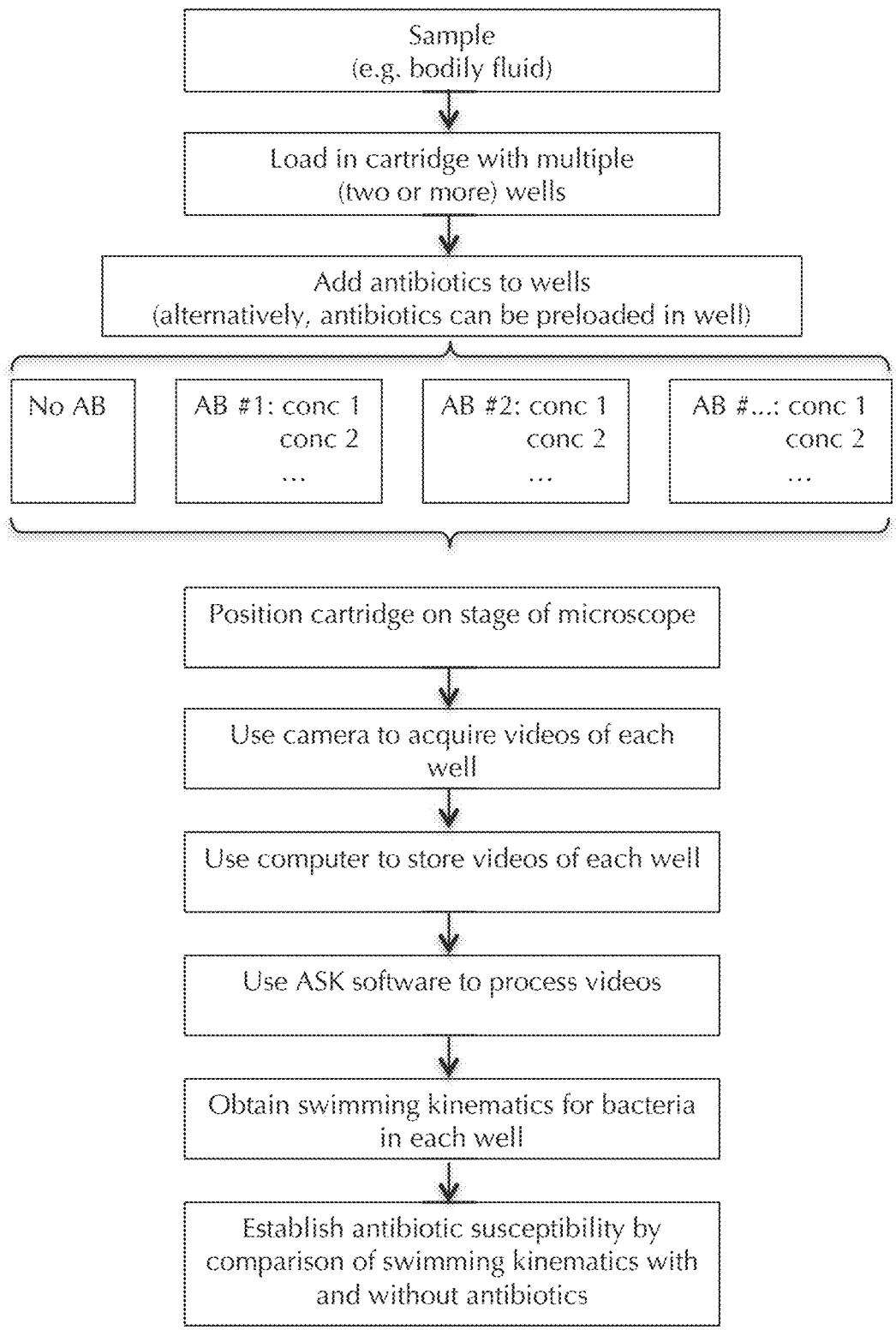

FIGS. 1, 4, 5, 6, 7, and 8 are block diagrams.
FIGS. 2, and 3 are flow diagrams.
FIGS. 9, 10, 16 and 21 are images.
FIGS. 11, 12, 13, 14, 15, 17, 18, and 19 are graphs.
FIG. 20 is a schematic side view of a cartridge.

We propose that using motility kinematics information (and corresponding techniques) for rapid microorganism (e.g., bacteria) detection (presence, absence, or counts), ID (i.e., identification), and AST (i.e., antibiotic or other antimicrobial susceptibility testing) (and other applications) can, among other things, for many microorganisms, result in a much shorter time-to-result, such as diagnostic results in the case of pathogens.

We use the term "microorganism" broadly to include, for example, any microbe or other organism of a microscopic or ultramicroscopic size. Microorganisms include bacteria, archaea, fungi, protists, eukaryotic organisms and other microorganisms.

We use the term "antimicrobial" broadly to include, for example, any material, element, component, substance, ingredient, or other matter, in any form, phase, capable of destroying or inhibiting or impairing or influencing the viability or the growth or the motility of one or more microorganisms, such as bacteria, archaea, fungi, protists, eukaryotic organisms and other microorganisms. including in particular pathogenic microorganisms. We sometimes use the word "antibiotic" interchangeably with the word "antimicrobial" used in its broad sense. We sometimes say that a microorganism is "susceptible" to an antimicrobial. We sometimes say that a microorganism is "resistant" to an antimicrobial. Among other things, antibiotics, antifungals, antibacterials, antiseptics, disinfectants, and detergents are and may be considered to be antimicrobials.

We use the term "AST" broadly to include, for example, antibiotic susceptibility testing or any testing of the susceptibility of a microorganism to any kind of antimicrobial.

Most current methods of AST of microorganisms, e.g., bacteria, require long testing times. This, in turn, is related to the metric that most methods are based on: the growth of bacteria and the disruption or reduction of this growth caused by exposure to antibiotics. Because a microbial generation lasts on average in the order of 30 minutes, and several generations can be necessary to obtain an accurate read-out, fast results are not attainable with this metric.

Pathogen identification (ID), especially in clinics, has been significantly expedited with the use of MALDI-TOF (Matrix Assisted Laser Desorption/Ionization Time of Flight) mass spectrometry, taking only minutes to report test results. However, sample preparation, which involves pathogen isolation and time-consuming culture-enrichment steps, takes at least a day before the actual ID test can take place.

We use the term "individual microorganism" to refer to a single individual (e.g., cell) of a species or strain, for example, a single *Escherichia coli* individual. Microorganisms include bacteria and other pathogens, among others. Similarly we use the terms "individual bacteria" or "bacterium" and "individual pathogen" and "individual microorganism" to refer to a single individual of a species or strain. We typically use the terms "microorganism" or "pathogen" to refer to a species or strain, and the terms "microorganisms" or "pathogens" or "bacteria" to refer to one or more species or strains. We sometimes use the term "species" broadly to include, for example, "strains". Pathogens and bacteria are considered to be types of microorganisms.

We use the term "motility" broadly to include, for example, any spontaneous movement of a pathogen or other microorganism, such as movement of an individual microorganism or movements of groups of individual microorganisms. Motility includes swimming and swarming motility through flagella; twitching and gliding motility through pili, fimbriae and other cell appendages; motility whose underlying locomotion mechanism is yet unknown; and other motilities.

We use the term "motility kinematics" broadly to include any features or properties of motion and movement strategies of a microorganism or groups of microorganisms within a medium such as a fluid or other sample or on a surface or near a surface. Such motion and movement strategies include, for example, swimming, swarming, twitching, or gliding. We sometimes refer to "swimming kinematics" as a good example of, and as a shorthand reference to, any kind of motility kinematics. Swimming kinematics include, for example, the trajectory, shape of trajectory, swimming direction, concentration of motile cells, speed, acceleration, mean square displacement, rate-of-turning, angle-of-turning, temporal sequence of different turning angles, diffusivity, net-to-gross-displacement ratio, curvature, fluctuations, ratio of motile and non-non-motile bacteria, and any quantities that can be derived from these, or in general from the trajectories of individual microorganisms, among other things. Motion and movement of a microorganism or groups of microorganisms can be substantially influenced by Brownian motion, i.e., the random movement of microscopic objects in fluids caused by thermal agitation. A commonly recognized influence of Brownian motion on a swimming microorganism are random deviations of the swimming trajectory from a straight path. The deviations are caused by collisions between the microorganism and the surrounding water molecules.

Motility, often mediated by appendages such as flagella or pili, is an advanced behavior possessed by many species of bacteria, in particular many pathogens, including *Escherichia coli, Pseudomonas aeruginosa, Vibrio cholerae* and other Vibrio strains, *Helicobacter pylori, Campylobacter jejuni, Salmonella typhimurium, Listeria monocytogenes, Acinetobacter baumannii, Borrelia burgdorferi* and other *Borrelia* strains, some *Bacillus* strains, *Bartonella* strains, *Clostridium* strains, *Legionella* strains, *Leptospira* strains, *Neisseria* strains, *Mycoplasma, Treponema*, among others. Pathogens that can be included in this analysis are not limited to human pathogens (including also food-borne pathogens), but also include pathogens of other organisms, in particular animals and plants. Motility comprises swimming motility in fluid, including motility in fluid adjacent to surfaces, as well as motility on surfaces, including among others twitching, gliding, and swarming motility. Because of the advanced cellular coordination required for motility, together with its dependence on both the physiological state and physical properties (e.g., size and shape) of a microorganism, (i) motility is characteristic of each species of bacteria (or other microorganism), and (ii) motility changes upon exposure to antibiotics and other chemicals and substances.

Some implementations of the motility techniques that we describe here are based on one or a combination of two or more of: (1) the generation, analysis, and maintenance of information about single-cell motility kinematics, e.g., swimming kinematics of microorganisms, (2) the quantification of motility to detect the presence, absence, or counts of individual microorganisms, (3) the quantification of motility kinematics for the identification of microorganisms, and (4) the detection of changes in motility of a microorganism as a biomarker for susceptibility to antibiotics or other antimicrobials.

For example, different bacteria have different swimming kinematics. For example, the enteric bacterium *E. coli* swims in a so-called run-and-tumble pattern in which nearly straight, approximately one-second long 'runs' are interrupted by reorientations ('tumbles') that are nearly random in direction. In contrast, many species of marine bacteria, including for example Vibrios, swim in run-reverse-and-flick patterns, in which a forward run is followed by a 180-degree reversal, followed by another 180-degree reversal and then a random reorientation ('flick'). Swimming kinematics can also be a function of a type of fluid, including the viscosity, chemical composition, nutrient content and temperature of the fluid or other material in which the microorganism is moving, or the properties of a surface on which or near which it is moving.

For some species of bacteria, some motility kinematics and other characteristic features of the individual microorganisms have been accurately characterized and quantified. For others, the motility patterns and kinematics and the characteristic features of the individual microorganisms can be characterized and quantified through imaging approaches at the resolution of an individual microorganism. The techniques for characterizing and quantifying that we describe here include the creation, maintenance, and use of a motility database of motility kinematics and a morphology database of characteristic features of the individual microorganisms that is part of a database management system in which each type of microorganism is associated with properties of its characteristic motility kinematics, including the trajectory, shape of trajectory, swimming direction, mean square displacement, concentration of motile cells, speed, acceleration, rate-of-turning, angle-of-turning, temporal sequence of different turning angles, diffusivity, net-to-gross-displacement ratio, curvature, fluctuations, ratio of motile and non-motile bacteria, and any quantities that can be derived from these, or in general from the trajectories of individual microorganisms, among other things. The techniques for characterizing and quantifying that we describe here include the creation, maintenance, and use of a morphology database of characteristic features of the individual microorganisms that is part of a database management system in which each type of microorganism is associated with properties of its characteristic features, including one or more of the shape, aspect ratio, convexity, area, size, direction of major axis, departure from spherical shape, intensity, distribution of intensity, or spatial arrangement relative to other individual microorganisms in the same sample. Additional characteristic features of individual microorganisms include expression of fluorescence, autofluorescence, fluorescent probes, binding to external agents such as micro- and nano particles, antibodies, quantum dots and other particles, which could be fluorescent or non-fluorescent.

We use the term "morphology" broadly to include, for example, any aspect of a form or structure of a microorganism or any of its parts or the spatial arrangement of an individual microorganism relative to other individual microorganisms.

Imaging of motility of an unknown microorganism moving in, e.g., a sample of bodily fluid, can thus be used in conjunction with the data stored in the motility database to rapidly (e.g., in a few minutes) identify which microorganism (if any) is in the sample, by comparing the motility kinematics properties derived from the images with known kinematic properties of known microorganisms stored in the database. In addition, susceptibility of a microorganism to an antibiotic or other antimicrobial can be determined rapidly by comparing the motility kinematic properties of the microorganism at one time or in one sample with motility kinematic properties of the microorganism at another time or in another sample derived from another set of images. For example, the other sample could be a sample of the same fluid but without the addition or with addition of a different concentration of antibiotic or other antimicrobial, or a sample of the same fluid in a different state or condition or at a different time.

Imaging of an individual cell (with or without a determination of the motility characteristics) of an unknown microorganism in a sample, for example, a bodily fluid sample, can also be used in conjunction with the data stored in the morphology database to rapidly (for example, in a few minutes) identify which microorganisms (if any) are in the sample, by comparing the characteristic features derived from the images with known characteristic features of known microorganisms stored in the morphology database. In addition, susceptibility of a microorganism to an antibiotic or other antimicrobial can be determined rapidly by comparing the characteristic features of the microorganism at one time or in one sample with characteristic features of the microorganism at another time or in another sample derived from another set of images.

In some examples, susceptibility of a microorganism to an antibiotic or other chemical or substance can be determined rapidly by comparing the Brownian motion of the microorganism at one time or in one sample with the Brownian motion of the microorganism at another time or in another sample derived from another set of images. For example, the other sample could be a sample of the same fluid but without the addition or with addition of a different concentration of antibiotic or other antimicrobial, or a sample of the same fluid in a different state or condition or at a different time. Because both the imaging of motility and the processing of motility image data to obtain quantitative properties of (or qualitative information about) motility kinematics are very rapid and can also be carried out in samples (e.g., direct patient samples) that have low counts of the microorganism, this approach is suitable to overcome a fundamental limit of traditional growth-based methods and thus deliver much more rapid results for presence/absence, counts, ID and AST of pathogens and other applications.

Our motility techniques use tracking of one or more individual bacteria or microorganisms as they move in a sample (we sometimes use the term bacteria as an example to refer broadly to any microorganism) and characterizing and measuring their motility kinematics. In brief, some implementations of our motility techniques include acquiring and processing microscopy videos of a sample, in some cases a bacterial suspension. In some cases, the bacterial suspension can be a bodily fluid, other fluid, a bacterial culture, or a fluid to which a microorganism has been added, or a fluid containing a sample having a solid or other non-fluid material, such as ground food, food particles, or an environmental sample, or a wound sample. In some cases, the bacterial sample need not be a fluid or need not be suspended in a fluid, but can be a solid or other non-fluid material. For microorganism (e.g., bacterial) identification (ID), in some applications, just the unknown sample is imaged and the resulting information used for comparison with information in the motility database and morphology database. For microorganism (e.g., bacterial) ID, in some applications, information on motility kinematics for at least two samples under different environmental conditions (e.g., temperature, pH) is compared. The morphology database and the motility database can in some instances be one and the same database and we sometimes use the simple term "database" to refer to one or the other or the combined database. Information in the morphology database and in the motility database can be dependent on other parameters, including parameters related to the conditions of testing (e.g., temperature, pH).

We sometimes use the term "fluid" broadly to include, for example, any medium or material of any phase in which a microorganism exhibits motility.

Typically, for AST, motility kinematics information about at least two samples is used, one with and one without addition of antibiotic. However, in some implementations, for AST, motility kinematics information about only one sample to which an antibiotic has been added is used, by comparing motility kinematics for the same sample at two or more times. (We sometimes use the term "antibiotic susceptibility testing" or AST broadly to include any analysis of the susceptibility of a microorganism to one or more antibiotics or other antimicrobials).

In some examples, the bacterial suspension is loaded into two or more (e.g., many) wells of a cartridge or other device to hold samples, in particular devices designed for high-throughput video microscopy, to test the susceptibility of the microorganism to one or more (e.g., many) antibiotic conditions (types of antibiotic, concentration of antibiotic, antibiotic exposure time, combination of antibiotics, or additional substances that supplement the antibiotics such as one or more enzyme inhibitors (e.g., a β-lactamase inhibitor), for example) in a single test, nearly simultaneously. To this end, a microscope equipped with an objective, a camera and optionally an automated stage and a temperature control system can be used. The camera acquires sequences of images of the bacterial suspension in each well. The image sequences can be acquired at a rate that captures a continuous movie of the motion of the bacteria (e.g., 15 frames per second; typically less for twitching motility). We refer to the image sequences as videos regardless of the frame capture rate.

In some implementations, image analysis software (part of what we call the ASK—Analysis of Swimming Kinematics—software) processes the image sequences to determine trajectories of individual microorganisms typically as fast as in near-real-time, or slower, depending on the computational resource. By "near-real-time" we mean, for example, almost at the same time as the videos are acquired, or with a delay of no more than a few seconds. From the trajectories, the software extracts quantitative metrics of motility kinematics, for example, swimming kinematics, including the speed, acceleration, rate-of-turning, angle-of-turning, mean square displacement, concentration of motile cells, temporal sequence of different turning angles, diffusivity, net-to-gross-displacement ratio, curvature, fluctuations, ratio of motile and non-motile bacteria, and any quantities that can be derived from these, or in general from the trajectories of individual microorganisms. The ASK software then performs either one or two or more of the following activities, and potentially others: (i) uses the extracted metrics of the swimming kinematics to detect the presence, absence or counts of individual microorganisms; or (ii) uses the extracted metrics of the swimming kinematics and known metrics of swimming kinematics stored in the motility database of the database management system to identify the bacteria (or other microorganism); or (iii) uses the extracted metrics of the characteristic features and known metrics of characteristic features stored in the morphology database of the database management system to identify the bacteria (or other microorganism); or (iv) determines the susceptibility of the bacteria to each antibiotic or other antimicrobial condition tested based, for example, on differences in swimming kinematics (inclusive of the effects of Brownian motion) of microorganisms in the samples exposed to different antibiotic or other antimicrobial conditions (including a complete absence of an antibiotic). Other applications for the swimming kinematics information are also possible.

Our motility techniques have broad applicability to detect (presence, absence, counts), identify, and determine the antibiotic susceptibility of any motile bacteria (or other microorganisms) present or prepared in any fluid in which it can move, for example, a liquid suspension, because our techniques focus on the analysis of motility kinematics as the biomarker for detection, ID and AST and for other applications. Examples of motile bacteria in clinical settings and food, agricultural and pharmaceutical industries include, but are not limited to: *Escherichia coli, Pseudomonas aeruginosa, Vibrio cholerae* and other *Vibrio* strains, *Helicobacter pylori, Campylobacter jejuni, Salmonella typhimurium, Listeria monocytogenes, Acinetobacter baumannii, Borrelia burgdorferi* and other *Borrelia* strains, some *Bacillus* strains, *Bartonella* strains, *Clostridium* strains, *Legionella* strains, *Leptospira* strains, *Neisseria* strains, *Mycoplasma, Treponema*, among others. Our motility techniques are applicable to bacteria that are motile through flagella in the fluid, including near surfaces, and also to bacteria that are motile on surfaces through other appendages, such as pili and fimbriae (e.g., twitching, gliding, and swarming motility). (Thus, when we refer to motility in a fluid we sometimes also are referring to motility near a surface or on a surface.)

Our motility techniques also have broad applicability for testing the susceptibility of microorganisms to any antibiotic or other antimicrobial, including antibiotics belonging to different classes (e.g., β-lactam or non-β-lactam) or, more broadly, any chemical or other substance to which a microorganism is susceptible in a way that affects its growth, viability or motility, including, but not limited to: Amikacin, Amoxicillin-clavulanate, Ampicillin, Ampicillin-sulbactam, Azithromycin, Azlocillin, Aztreonam, Aztreonam-avibactam, Besifloxacin Biapenem, Carbenicillin, Cefaclor, Cefamandole, Cefazolin, Cefdinir, Cefditoren, Cefepime, Cefetamet, Cefixime, Cefmetazole, Cefonicid, Cefoperazone, Cefotaxime, Cefotetan, Cefoxitin, Cefpodoxime, Cefprozil, Ceftaroline, Ceftaroline-avibactam, Ceftazidime, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycinf, Colistin, Dalbavancin, Daptomycin, Dirithromycin, Doripenem, Doxycycline, Enoxacin, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicink, Grepafloxacin, Iclaprim Imipenem, Kanamycin, Levofloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Telavancin, Telithromycin, Tetracycline, Ticarcillin, Ticarcillin-clavulanate, Tigecycline, Tobramycin, Trimethoprim, Trimethoprim, Sulfamethoxazole, Trospectomycin, Trovafloxacin, Ulifloxacin (prulifloxacin), Vancomycin.

Our motility techniques also have broad applicability for testing the susceptibility of microorganisms to other substances, including substances that are not classified as antibiotics but are known or hypothesized to have effects on microorganisms including effects that are similar to the effects of antibiotics. Some examples are antiseptics. Some examples are detergents. One example is natural products such as cranberry juice. Our motility techniques have broad applicability for testing the effect of any substance on the motility of microorganisms. Our motility techniques are also applicable to combinations of two or more antibiotics or other substances including enzymatic inhibitors (e.g., β-lactamase inhibitors), possibly combined with other motility affecting factors, including, but not limited to, fluid types, fluid properties (e.g., viscosity), chemicals (e.g., nutrient supplement, toxins), and temperature. All of these examples are within the scope of the terms "antimicrobial" or "antibiotic" as we use those terms in their broadest senses.

Multiple mechanisms can cause changes in the swimming kinematics of bacteria upon antibiotic exposure. One mechanism is a change in the mechanics of swimming. For example, β-lactam antibiotics (e.g., penicillin, penem or cephem classes) that inhibit cell wall biosynthesis cause changes in cell shape (see for example FIG. 21), which in turn directly affects how the cell swims. A second mechanism is biochemical. Non-β-lactam antibiotics (e.g., aminoglycoside, quinolone or tetracycline classes) inhibit protein, DNA or RNA synthesis, which adversely impacts the pathogen's physiological state, which is often a determinant of motility.

Some implementations of our motility techniques can use elements, devices, technologies, and combinations of them described below. A wide variety of other implementations are also possible.

As shown in FIG. 1, and more specifically in FIG. 20, in some implementations, a cartridge 10 having multiple (2 to 1000; for example, 100) wells 12 is used to contain the bacterial suspension (or "sample") 14 in the wells for imaging. In some cases the wells are approximately 4 mm×4 mm×2 mm (but dimensions can vary), so that many wells fit on a small cartridge (for example, the size of a microscope slide or a 96-well plate). The wells can have any shape such as square or circular or oval or rectangular or rectangular with rounded edges, among others, and any height. Typical heights can be, for example, from 10 µm to 10 mm. The use of many wells allows high-throughput in AST (enabling many antibiotics, or many antibiotic conditions, or many samples, or combinations of these, to be tested in respective wells), for example, following the concept of the broth dilution method to test the different concentrations. The user can use as many of the wells as needed for a particular test. Different cartridges can also have different numbers of wells. Different wells of a given cartridge need not all have the same sizes, shapes, heights, or configurations, but one or more of those parameters can differ between different wells of the cartridge. Although only two wells are shown in FIG. 20, actual cartridges will typically have more than two wells.

The techniques that we describe for loading, containing, imaging, and analyzing one or more samples, can be applied to any kind of well as used in its broadest sense.

We use the term "well" broadly to include, for example, any container, receptacle, reservoir, compartment, recess, microfluidic or other channel, chamber, holder, surface, containment device, or other device that holds, contains, protects, isolates, or otherwise separates a sample from another sample or from the environment. We sometimes use the word "channel" interchangeably with the word "well" as used in its broadest sense.

For pathogen ID purposes, a minimum of one well is required. In some instances, it may be possible to use a minimum of two wells to compare the motility kinematics between two fluid samples under different environmental conditions at approximately or exactly the same time. For pathogen AST purposes, typically a minimum of two wells is used if the user intends to compare the motility kinematics between two fluid samples (e.g., one with and one without an antibiotic or other antimicrobial) at approximately or exactly the same time. In some instances, it may be possible to compare, for example, motility kinematics of a sample in a well to motility kinematics for the same microorganism stored in the motility database. In some instances, it may be possible to compare, for example, motility kinematics of a sample in a well to motility kinematics obtained and stored for the same well at an earlier time point.

In addition to each well using only a small amount of space on the cartridge, the smallness of the wells reduces the amount of sample required for analysis, which is particularly beneficial when only low-volume samples are available, such as certain bodily samples. The smallness of the wells also reduces residual fluid flows within each of the wells. Such residual fluid flows (that is, small movements of the fluid that occur even if, for example, a user is not deliberately causing them) are known to occur when a liquid is contained in a large well or a well with a free surface, for example due to uneven temperature distributions. Reducing or avoiding these flows helps reliable tracking of bacteria, because in the presence of such flows the analysis of swimming kinematics of bacteria is confounded by the movement of the fluid. Nevertheless, if the motility kinematics of bacteria are confounded by the presence of residual fluid flows and the magnitude of these residual flows is modest, the ASK software can take this into account and determine the motility kinematics of the bacteria by subtracting the contribution of the flow to the movement of the bacteria. To reduce the influence of residual flows, in some examples, the cartridge is sealed with a membrane or other cover 16 (e.g., a breathable cover to allow gas passage) after filling the wells. In some cases, the cover could (i) be present on the cartridge prior to filling (for example to ensure sterility), (ii) be peeled off temporarily by the user for filling the wells and then reapplied, or (iii) remain in place and be perforated during sample injection using a needle.

We use the term "cover" broadly to include, for example, any membrane, layer, sheet, surface, or other device that overlays, protects, isolates, or otherwise separates an interior of a well from the environment. We sometimes use the word "membrane" interchangeably with the word "cover" as used in its broadest sense.

To avoid immobilization of swimming bacteria due to attachment to the surfaces of the wells or to the sealing cover, the surfaces of the wells or the sealing cover or both can be formed of materials or pre-coated 18 with chemicals (e.g., bovine serum albumin, or PLL-g-PEG or PLL-g-PMOXA) or both to prevent attachment of bacteria to those surfaces. In some cases, for example when it is desirable to look at motility on surfaces, the surfaces of the wells can be made of materials or pre-coated with chemicals that favor attachment of bacteria to those surfaces (e.g. PLL).

The respective wells on the cartridge can house subportions of one sample or multiple different samples (for example, a single sample divided among multiple wells, or different samples in different wells, or combinations of those) and these can be exposed to one or multiple antibiotics or other antimicrobials (for example, one antibiotic in multiple wells, or different antibiotics in different wells, or multiple antibiotics in particular wells, or combinations of those) having one or multiple antibiotic conditions (e.g., concentrations, different antibiotic combinations) (for example, one antibiotic condition in multiple wells, different antibiotic conditions in different wells, or combinations of those). In some examples, a single sample (e.g., bodily fluid) is filled into two or more of the wells and exposed to a range of different antibiotics at different concentrations (one antibiotic and concentration for each well). Replicated wells can also be used (same sample and antibiotic conditions in more than one well).

In some applications, a user loads the sample or samples into the wells, for example through a pipette (e.g., the same sample goes into all the wells). Options include, for example, loading from the top (for example, well-by-well or multiple wells simultaneously with a multi-channel pipettor or a robotic system) or injecting into a main reservoir from which built-in fluidics or other fluid distribution system take the sample into individual wells.

In some implementations, the cartridge can be pre-loaded with a predetermined set of antibiotics at predetermined concentrations or other conditions in different wells, to which the user adds the sample or samples. The pre-loaded antibiotics can be lyophilized.

In some implementations, the user adds both the antibiotic or antibiotics and the sample or samples to the wells.

In some implementations, the user adds the antibiotic or antibiotics and the sample or samples to the wells sequentially, or vice versa (sample or samples first, then antibiotic or antibiotics).

A cover that seals the wells of the cartridge can be used to maintain sterility. The cover is typically transparent as is the cartridge. The cover could for example be gas-permeable. The cover could for example be removable. The cover could for example be flexible or rigid. The cover could for example be flat or patterned. The cartridge could for example come with the cover applied, which the user can transiently remove for filling, before resealing. The cover could for example be made of a material that is easy to puncture with a needle for filling. The cover could for example be made of a solid material. The cover could for example have one or more holes. Other types of covers are also possible.

In some instances, the purpose of AST is to test the susceptibility of bacteria to a range of conditions of one or multiple antibiotics.

In some implementations, a user adds the desired antibiotic or antibiotics or other antimicrobials, each at the desired condition or conditions (e.g., concentration), in each well. The desired antibiotic is usually prepared in a liquid stock solution. For some antibiotics, the antibiotic can also be added in a powder form, for example when storing a liquid stock is an issue.

In some implementations, the antibiotic or antibiotics are pre-loaded on the cartridge, within reservoirs. Fluidics built into the cartridge or other fluid distribution system then automatically deliver the appropriate concentrations of the antibiotic or antibiotics to the individual wells.

In some implementations, the antibiotic or antibiotics are pre-loaded on the cartridge in the individual wells, with each well potentially having a different concentration of a given antibiotic or antibiotics. Bacteria are thus exposed to the antibiotic when they are loaded onto the wells by the user.

Combinations of two or more of the above techniques for loading the cartridge can also be used.

As shown in FIG. 1, in some cases, the cartridge is positioned on the motorized stage 20 of an optical microscope 22 for imaging and tracking (we use the term "tracking" to refer to determining the trajectory) of bacteria. The fundamental elements of the microscope are (i) an objective, (ii) (optionally) an automated moving stage 20, and (iii) (optionally) a temperature control unit 24. In some cases, the position of the cartridge can be fixed and the imaging system (typically composed of objective and camera) can move from well to well. In some cases the microscope can have multiple imaging systems (e.g., multiple objectives and cameras) to acquire multiple videos of either the same well or of different wells, either simultaneously or non-simultaneously. Other combinations are possible.

The automated moving stage enables the microscope, under control of a computer program through a device operation layer 34, to accomplish any one or a combination of two or more of the following: (i) move from well to well horizontally in the cartridge, so that each well or selected sets of wells can be imaged in turn; (ii) scan different positions vertically or horizontally in any given well, in order to obtain more data for that well; or (iii) image the bottom surface of the well, for example to track bacteria that move by surface motility, such as twitching, gliding or swarming motility. The stage typically has an accuracy of a few micrometers.

The objective can have any magnification. Typical magnifications are 10× or 20×, but other magnifications are possible.

A temperature control unit 24 can be used to maintain samples at, for example, normal body temperature (typically 37° C.). The temperature control unit typically has a temperature-controlled insert mounted on the stage of the microscope or a temperature-controlled enclosure that surrounds the cartridge, or the stage or the whole microscope or the whole device.

Different types of microscopy techniques can be used. Phase-contrast microscopy is typically used, but dark-field microscopy, bright-field microscopy, fluorescence microscopy, or other microscopy techniques can also be used.

The motion of the cartridge on the stage of the microscope is controlled by a computer through dedicated software 28.

Connected to the microscope is a camera 30 used to acquire videos (i.e., sequences of images) of the sample in each well. The camera typically has a black-and-white sensor or a color sensor. In some implementations, the sensor can have a resolution of 5 µm to 20 µm per pixel and between 500×500 and 2000×2000 pixels (other specifications are also possible). A sequence of images is composed of two or more images, but in some implementations it could be a single image.

In some cases, imaging is performed at a rate of 15 frames per second, although slower rates (e.g., 1 frame per second or 5 frames per second) or faster rates (e.g., 100 frames per second) are possible, depending on the sample and the type of motility being tracked.

In some cases, one video is acquired per well (or sometimes multiple videos at multiple positions within each well). The video typically lasts between 1 and 30 seconds, which typically is a time sufficient to obtain motility kinematics information from trajectories of the bacteria. Videos can also be shorter than 1 second or longer than 30 seconds in some cases.

In some cases, the duration of each video can be adaptive. For example, the software (see below) processes each video in near-real-time (that is, providing swimming kinematics almost at the same time as the videos are acquired, or with a delay of a few seconds), decides if motility kinematics have been reliably quantified, and continues video acquisition until sufficient data for reliable quantification of motility kinematics have been acquired, up to a maximum time (for example, 5 minutes, but can be as long as 30 minutes or more).

In some implementations, the resolution of each image can be made adaptive by adjusting the binning (i.e., combining adjacent pixels) in the camera settings. In these implementations, the software adjusts (typically lowers) the image resolution if faster readout is required. The size of the bacteria in a sample and their motility kinematics are important criteria for setting image resolution and thus binning (e.g., microorganisms with fast motility speeds can be tracked with lower image resolution).

In some implementations, the size of each image (i.e., field of view) can be made adaptive depending on the concentration of bacteria in a sample. Taking images of a small field of view, for example, is sufficient to quantify swimming kinematics of bacteria in a sample that has a high cell concentration.

The same software installed on the computer controlling the microscope can be used to control the camera.

A computer stores the videos acquired by the camera in a temporary data storage unit 40 (e.g., a RAM). Typically, the same software installed on the computer controlling the microscope and the camera can be used to control the storage of the videos.

In some implementations, the procedure produces one video (i.e., sequence of images) per imaging position (if there are multiple imaging positions in each well) per well. Each video (i.e., all images in that video) is stored. Suitable labeling scheme and directory structure are used. Storage of the images can occur in different formats, for example jpeg or tiff formats. Videos can also be directly stored in different formats, for example avi format. Videos can be uncompressed. Videos can be compressed with a video codec, for example H.264/MPEG-4 AVC. Other compression methods are included.

Figure 9:
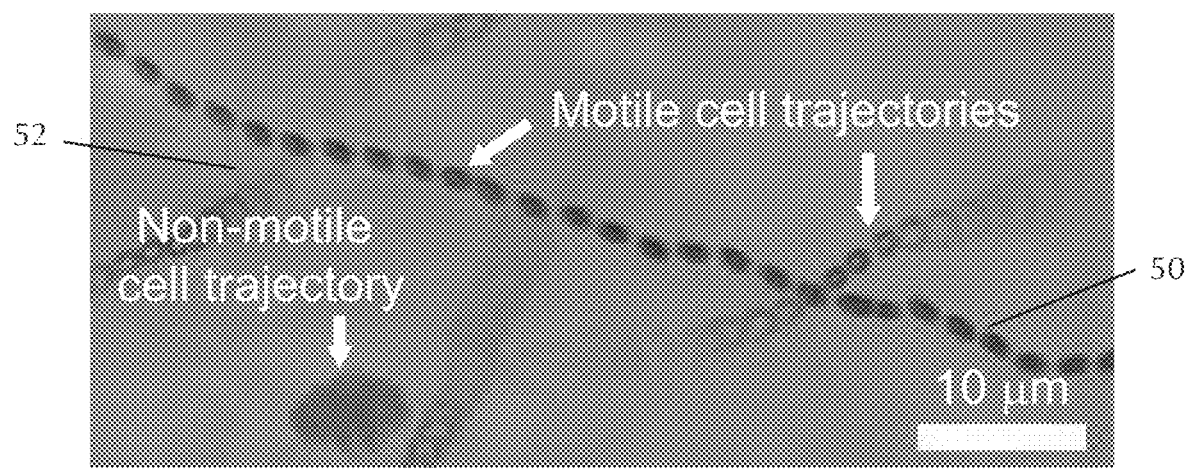

The ASK software 42 processes the videos, computes trajectories of bacteria and analyzes the swimming kinematics of individual bacteria in a sample. In some implementations, a pre-screening step can be included, in which one or more wells, for example an antibiotic-free well, is imaged to obtain an initial assessment of motility, for example to rapidly (for example, in real time) determine the presence of motile bacteria through image analysis techniques. Some examples of image analysis techniques for this purpose use a minimum-intensity projection as shown in FIG. 9 (e.g., suitable for images with a white or otherwise light background); some examples use a maximum-intensity projection (e.g., suitable for images with a black or otherwise dark background). In these approaches, a minimum (or maximum) intensity projection image is created in which each pixel is given the minimum (or maximum) intensity that that pixel has across all images in the video. In this manner, bacterial trajectories appear as streaks 50, 52 that often make motility or changes of motility immediately apparent. The ASK software determines the presence of motility in a given sample by identifying these streaks in a minimum (or maximum) intensity projection image. This information can be obtained very rapidly and can be used to interrupt or otherwise adjust the workflow or stimulate motility by changing environmental conditions (e.g., adding chemical substances such as Ethylenediaminetetraacetic acid (EDTA)) if no or very few motile bacteria are present. The pre-screening step can be included optionally by the user. The minimum or maximum intensity projection approaches are only examples of a much wider range of image analysis techniques to obtain motility kinematics from the videos.

Figure 4:
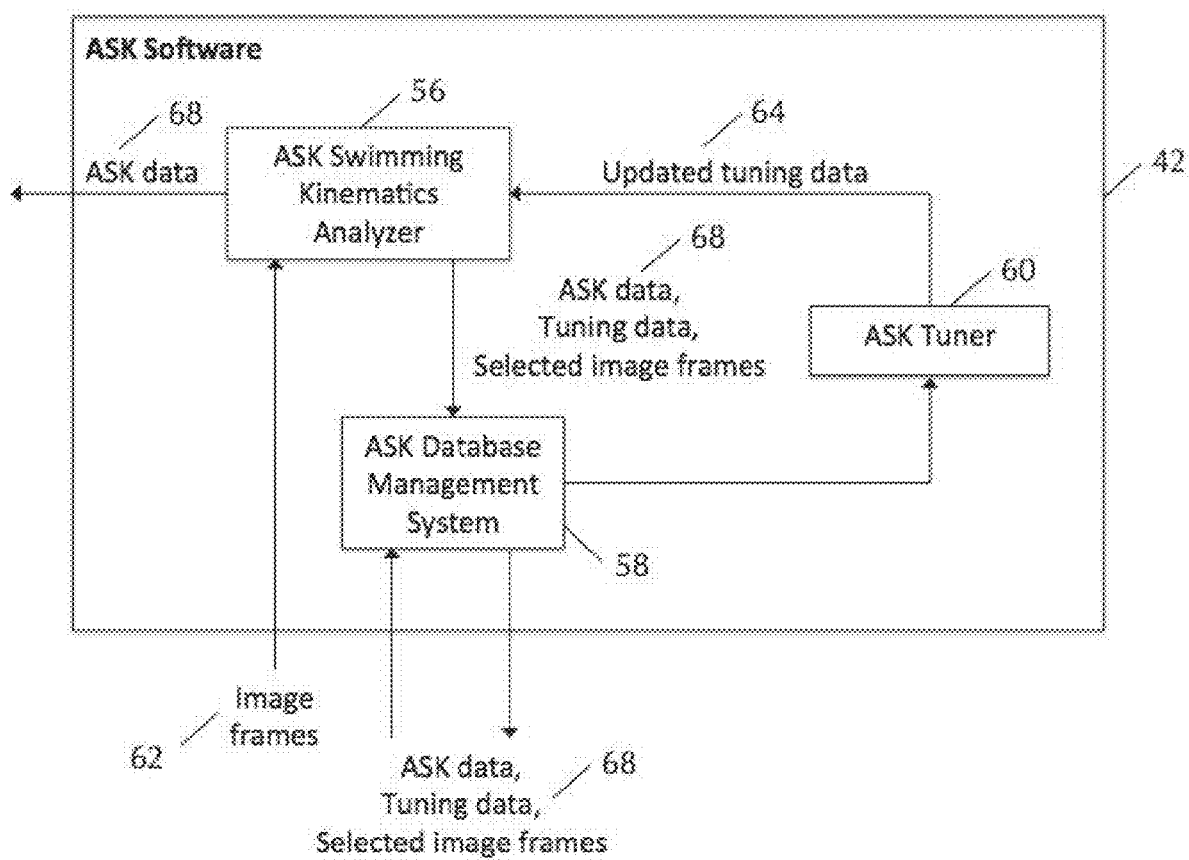

As shown in FIG. 4, the ASK software includes three main components: a swimming kinematics analyzer 56, an ASK database management system 58 that includes the motility database among other things, and an ASK tuner 60. If motile bacteria are present in the sample as determined by the pre-screening step (as discussed with respect to FIG. 9), the swimming kinematics analyzer (see also FIG. 5) in the ASK software performs image and data analysis routines on image data ("image frames") 62 from the temporary storage 63 (FIG. 5), and on updated tuning data 64 (e.g., parameters used for bacterial detection and tracking) from the ASK tuner 60 (if previous measurements exist), to (i) find individual bacteria in each image of a video using a bacterial detector 70 (see also FIG. 6), (ii) connect individual bacteria from image to image in a video for tracking and reconstructing their trajectories using a bacterial tracker 101 (see also FIG. 7) and (iii) obtain swimming kinematics data of bacteria using the ASK data generator 103 (see also FIG. 8). The swimming kinematics analyzer 56 produces ASK data and tuning data 68 that is stored in the ASK database management system 58. Selected image frames 62 (e.g., subset of a video or the whole video) can be also stored in the ASK database management system 58.

Figure 6:
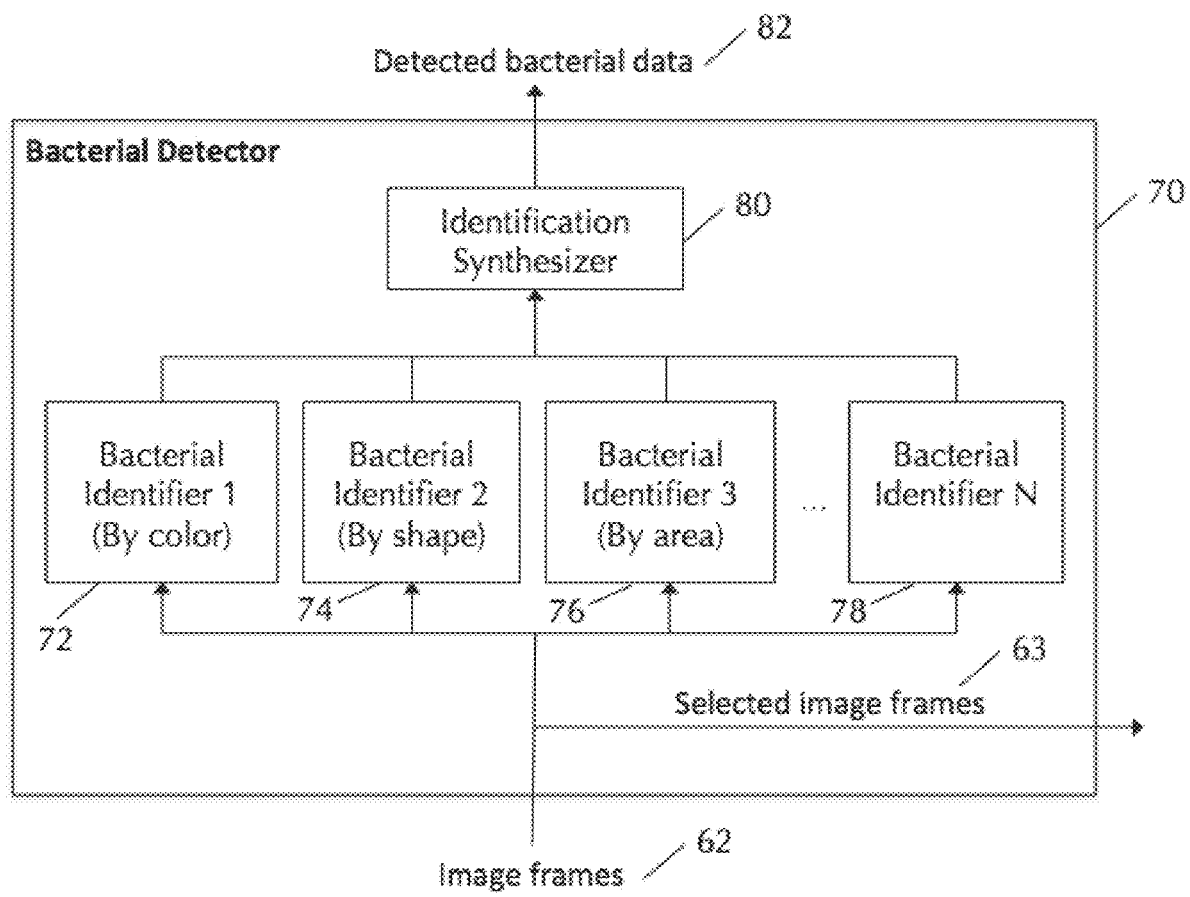

As shown in FIG. 6, in some examples, individual bacteria are detected in each image frame using multiple bacterial identifiers based on image analysis techniques. These include, but are not limited to, color identification 72 (e.g., pixel intensity gradient), shape identification 74 (e.g., aspect ratio, convexity), area identification 76 (e.g., size threshold) and potentially a broad range of other identifiers 78. These identifiers can be applied either in sequence or in parallel, and both with and without weighting each identifier, by an identification synthesizer 80 to produce detected bacterial data 82. In some cases, any two of the identifiers can be used in combination without the third. The bacterial detector can use both original images (i.e., raw) or processed images to identify bacteria. One example of processed images are images that result from subtraction of a background image, where the background image could be computed as the mean or median image of the image sequence, for example, or the initial image in the sequence, for example.

In some implementations, information on a bacterium will be stored in a data structure in the database management system including attributes determined for that bacterium, including its horizontal and vertical location, its size, its intensity, its shape, the direction of its major axis (if elongated), any other departure from spherical shape, the distribution of its intensity, the spatial arrangement relative to other bacteria in the sample, and any other parameter that can be obtained from its image.

Figure 7:
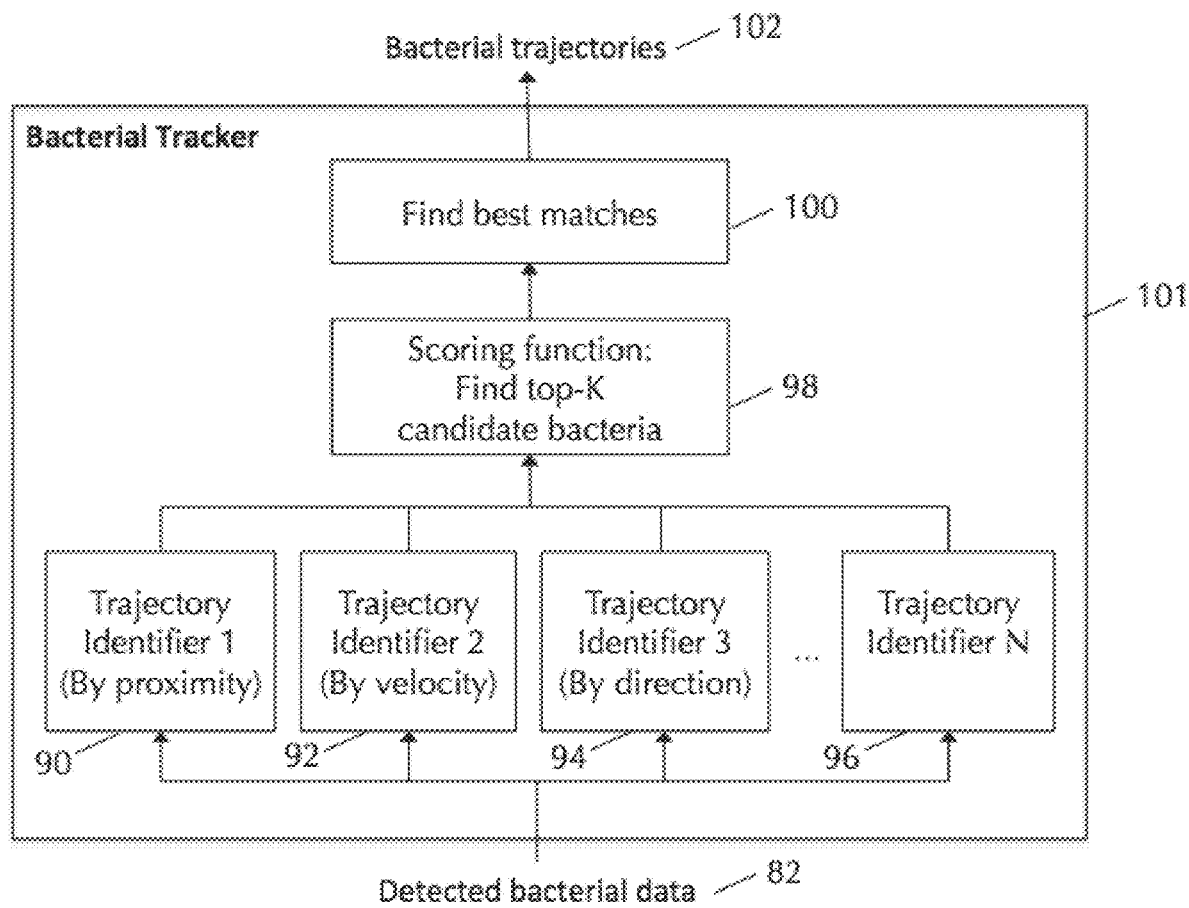

As shown in FIG. 7, individual bacteria are tracked from image frame to image frame based on the detected bacterial data 82 (e.g., coordinates, area, shape) using tracking techniques in the bacterial tracker 101. By tracked, we mean that the data of an individual bacterium detected in a frame are associated with the data for the same individual bacterium in other frames. For example, for a given bacterium detected in a given image frame, the currently detected bacterium is assigned to a previously identified trajectory within a search radius by one or more trajectory identifiers based on proximity 90 of positions (one example being the nearest-neighbor approach with a certain backtracking depth), velocity 92, direction 94, and acceleration, and a range of other criteria 96. The search radius can be defined by the user or adaptively set by the software (e.g., the ASK tuner 60) based on previous tracking information stored in the database of the ASK database management system. The currently detected bacterium is assigned to a new trajectory if there is no previously identified trajectory within the search radius. A scoring function that utilizes one or more of the criteria described above is then used to determine the best match 100 among a certain number of candidate bacteria based on a scoring function 98 and thus link bacterial positions in consecutive frames into the trajectory 102 of a given bacterium. The criteria to link bacteria into trajectories can be probabilistic.

The identified swimming trajectories can be used to obtain a count of the number of motile bacteria in the sample. The identified Brownian motion trajectories can be used to obtain a count of the number of non-motile bacteria in the sample. Because the imaging volume is known, this count can be converted into a concentration of motile bacteria or non-motile bacteria or both.

Information derived from the tracking process can include the presence, absence, count, percentage or concentration (or combinations of those categories) of motile bacteria in the sample, which can provide measures of, for example, the existence, nature and potential severity of an infection. Absence of motile bacteria or other pathogens can also for example help support the conclusion that an infection is viral in origin, as opposed to bacterial. The change over time in the number of motile bacteria or the change over time in the fraction of motile versus non-motile bacteria can provide information on the susceptibility of bacteria to a given antibiotic. The cell concentration can be then utilized with information on microorganism identity (ID), described below.

In some implementations, criteria can be used to eliminate from analysis non-swimming particulates or other entities present in the sample. Particulates or other entities that are not microorganisms are often present in samples and can be of biological or non-biological origin or both. Criteria utilized to eliminate them from analysis include size, shape, movement (for example, absence of movement for particulates or other entities that are surface-attached), and others, and combinations thereof. Elimination of particulates or other entities from analysis can be useful to simplify the analysis, in particular for turbid samples.

Swimming kinematics are typically quantitative features of the motion and trajectories of bacteria, computed at the level of individual bacteria, and sometimes averaged over all or a subset of the bacteria imaged in a sample.

Figure 8:
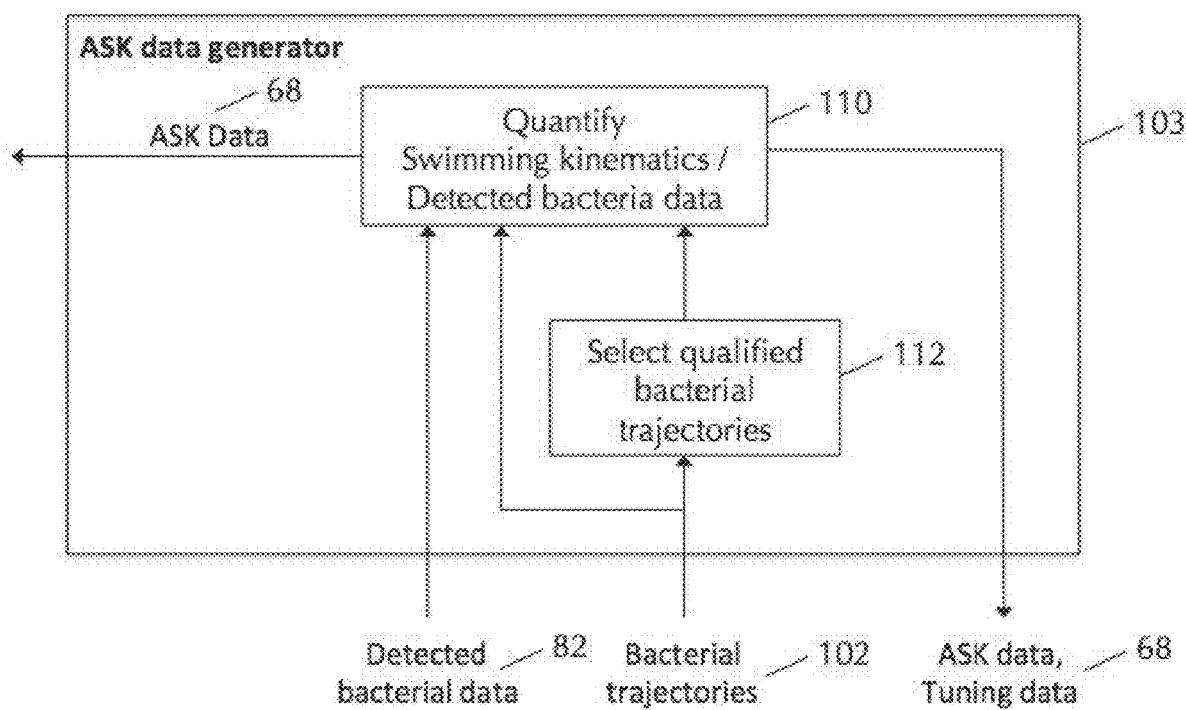

As shown in FIG. 8, the swimming kinematics of individual bacteria are aggregated and analyzed statistically 110 in the ASK data generator 103 in one of two modes: (i) using all the tracked trajectories, or (ii) using selected trajectories 112 that satisfy certain user-defined criteria, such as criteria on the length of the trajectory, the total distance moved, the speed, and so on. The aggregation of data can apply to a few, tens, hundreds, or thousands of individual bacteria by a variety of mathematical processes such as a simple mean of the values of a given attribute.

In some implementations, the ASK data 68 can include the following swimming kinematic features.

1. Speed. Speed is obtained from the trajectory of individual bacteria for example by dividing the absolute distance traveled (along the trajectory) by the duration of the trajectory.
2. Acceleration. Acceleration is obtained from the trajectory of individual bacteria for example by measuring the change in speed along the trajectory.
3. Turning rate. The turning rate, also known as the tumbling rate, is obtained from the trajectory of individual bacteria for example by defining a criterion for turning (for example, a change in direction above a certain threshold angle in a given time interval, possibly accompanied by a decrease in instantaneous swimming speed below a certain threshold), identifying all turning events in a trajectory, and dividing the number of turning events by the duration of the trajectory.
4. The angle of turning. The angle of turning is obtained from the trajectory of individual bacteria for example by first identifying a turn (using the same criteria described in point 3 above) and then determining the change in direction between the direction before a turn and the direction after a turn.
5. The overall motility pattern or "shape" of the trajectory. The alternation of different components of a trajectory, with a certain 'tempo' (e.g., nearly straight runs, turns, reversals, stops) is characteristic of a given species and represents its motility pattern.
6. The diffusivity of bacteria, computed as the area covered over a given time. The diffusivity represents a measure of the overall area covered by the bacterium in its motion.
7. The net-to-gross-displacement-ratio (NGDR) of the bacteria, computed as the linear distance traveled from the start to the end point of a trajectory, divided by the distance traveled along the trajectory itself. The NGDR represents a measure of how straight (vs. tortuous) a trajectory is.
8. The mean square displacement (msd) of the bacteria, computed as the square of the linear distance traveled in a given time period.
9. The curvature of the trajectory, which is obtained for example by determining the change in direction during swimming.
10. The fluctuations around the main movement pattern ('wobble').
11. The change in the fraction of motile vs. non-motile bacteria over time.
12. Quantities derived from the combination of these swimming kinematics or otherwise derived from the analysis of trajectories.

Swimming kinematics are characteristic of each species of bacteria, providing a strong criterion for pathogen identification. For example, *E. coli*, a well characterized model organism for studies of bacterial motility, swims in a so-called 'run-and-tumble' motility pattern by alternating straight swimming with occasional turning in a nearly random direction (FIG. 10a,b). On the other hand, *P. aeruginosa* primarily swims back-and-forth, in a so-called 'run-and-reverse' motility pattern (FIG. 10c,d).

Figure 10:
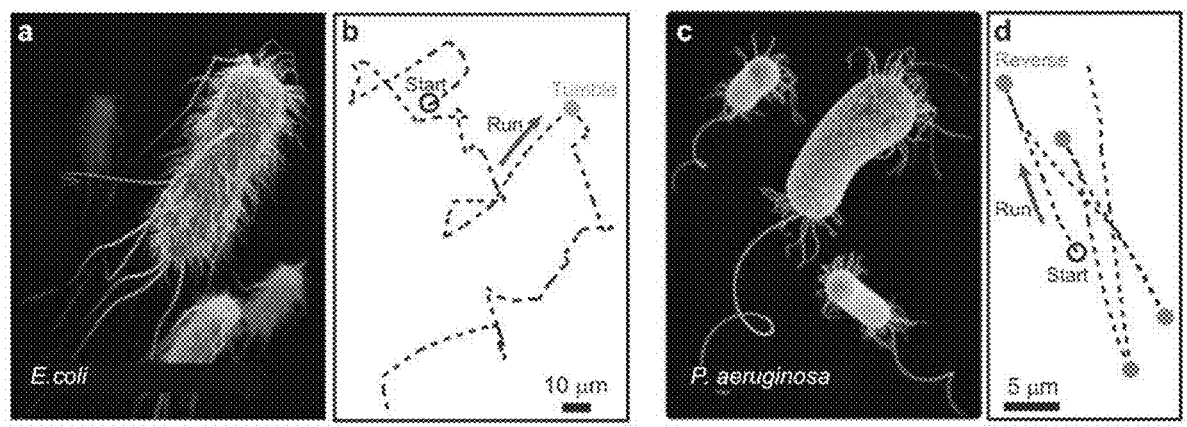

In some implementations, for purposes of identifying a microorganism, swimming kinematics obtained from each well are compared 130 (see FIG. 2) by the ASK software with known swimming kinematics data for known microorganisms stored in the motility database. If the measured swimming kinematics are sufficiently close to the known swimming kinematics stored in the motility database, a positive ID of the microorganism is established. By "sufficiently close" we mean that a statistical analysis is performed and a confidence level is established for the positive identification of the microorganism. An example criterion for *E. coli* and *P. aeruginosa* is the turning angle, which is characteristically different (FIG. 10). The most robust, potentially multi-parameter criterion for ID (e.g., a combination of speed, turning angle, and turning rate) is determined as part of the analysis. FIG. 10 shows *E. coli* (FIG. 10a) swimming in a 'run-and-tumble' motility pattern (FIG. 10b), and *P. aeruginosa* (FIG. 10c) swimming in a 'run-and-reverse' motility pattern (FIG. 10d). FIGS. 10a and 10c are adapted from the Center for Disease Control and Prevention (CDC), 'Antibiotic Resistance Threats in the United States', 2013.FIG. 10b is adapted from H. Berg, '*E. coli* in motion', Springer 2004. In some implementations, for purposes of identifying a microorganism, characteristic features of individual microorganisms detected from each well are compared 130 (see FIG. 2) by the ASK software with known characteristic feature data for known microorganisms stored in the morphology database. If the measured characteristic features are sufficiently close to the known characteristic features stored in the morphology database, a positive identification of the microorganism is established. By "sufficiently close" we mean that a statistical analysis is performed and a confidence level is established for the positive identification of the microorganism. An example criterion for bacilli and cocci is the cell shape, which is characteristically different: bacilli have the shape of rods, cocci have the shape of spheres. Vibrios have yet a different, crescent-like shape, We interpret morphology broadly, as comprising also the spatial arrangement of an individual microorganisms relative to other individual microorganisms. An example is represented by *Staphylococcus* spp. and *Streptococcus* spp., whose spatial arrangement is characteristically different: *Staphylococcus* spp. forms grape-like clusters, *Streptococcus* spp. forms chain-like clusters. Spatial arrangement thus provides an additional criterion for ID. The most robust criterion, which is potentially a multi-parameter criterion (for example, a combination of motility, size, shape, and spatial arrangement), is determined as part of the analysis. In some implementations, characteristic features of individual microorganisms pertaining to both motility and morphology are used for purposes of identifying a microorganism.

The motility data stored in the ASK database management system is constructed from known swimming kinematics obtained previously, for example from fresh clinical isolates, clinical stock isolates, other isolates, challenge organisms available from the Center for Disease Control and Prevention (CDC), or standard reference strains for quality control set by the Clinical & Laboratory Standards Institute (CLSI) or other institutions, among others. This pre-acquired data is stored in the motility and the morphology database within the computer that runs the ASK software or available online for rapid access, for systems connected to the Internet. The accuracy of the comparison can be enhanced through the creation of databases covering multiple conditions (e.g., one database per infection or per bodily fluid) and the use of multi-parameter comparison criteria (e.g., comparison of both swimming speed and turning rate). The ASK software also determines the statistics of the comparison (i.e., whether statistically significant and at what level of significance), providing metrics of confidence in the identity of the pathogens or other microorganisms. Furthermore, the software can identify multiple species of pathogens in samples that contain multiple species of pathogens and provide statistical metrics of the confidence in the identification of each. Furthermore, the software can identify multiple genotypes within a single bacterial species in samples. For example, the co-occurrence of two genotypes differing in their antibiotic susceptibility will be evident from a bimodal distribution of motility kinematics.

The swimming kinematics change upon exposure to antibiotics, providing a biomarker for AST. AST can be performed in one of two ways, or a combination of them: without or with use of a reference database. As shown in FIG. 2, in some cases, the ASK software performs a comparison 130 of the swimming kinematics measured 132 in the presence of an antibiotic with the swimming kinematics measured in the absence of the antibiotic, on the same cartridge. The software also determines the statistics of the comparison (i.e., whether statistically significant and at what level of significance), providing metrics of confidence in the susceptibility of the pathogen to the antibiotic.

In some cases, the comparison is done based on a set of quantitative criteria defined and stored a priori. To achieve this, a database of how the swimming kinematics of a single microorganism are known to change upon exposure to antibiotics is used. One database per target pathogen or other microorganism is used: for each, the changes in the multiple parameters defining the pathogen's swimming kinematics (e.g., speed, turning angle, turning rate, or motility pattern, mean square displacement, among others) are quantified, for different antibiotics, different conditions (e.g., different temperatures, different chemical compositions of the sample), and different exposure times. This database then serves as the yardstick to define a set of quantitative criteria, including both absolute and relative changes, to determine antibiotic susceptibility of bacteria in a given sample during diagnostics. The software also determines the statistics of the comparison (i.e., whether statistically significant and at what level of significance), providing metrics of confidence in the susceptibility of the pathogen to the antibiotic.

Figure 19:
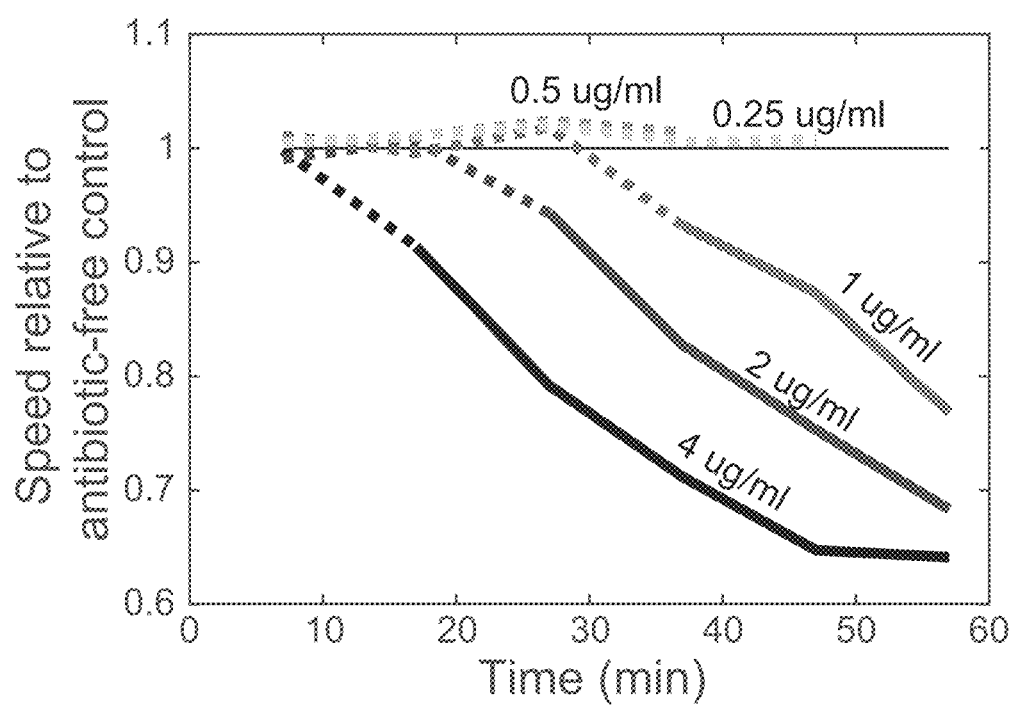
Figure 20:
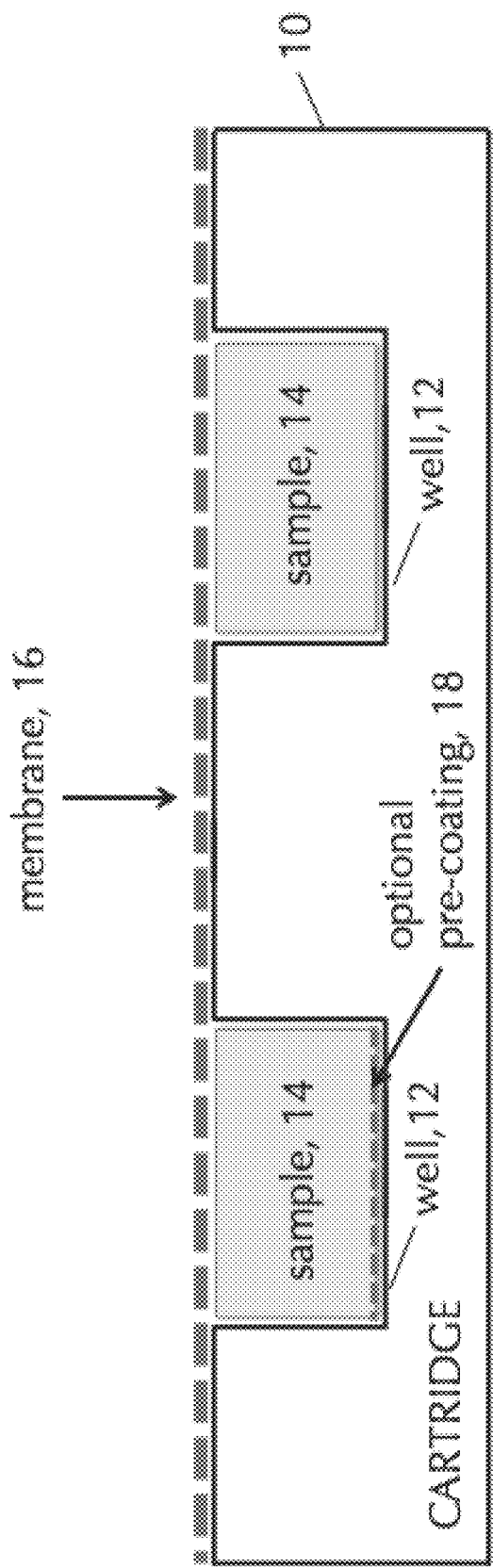
Figure 21:
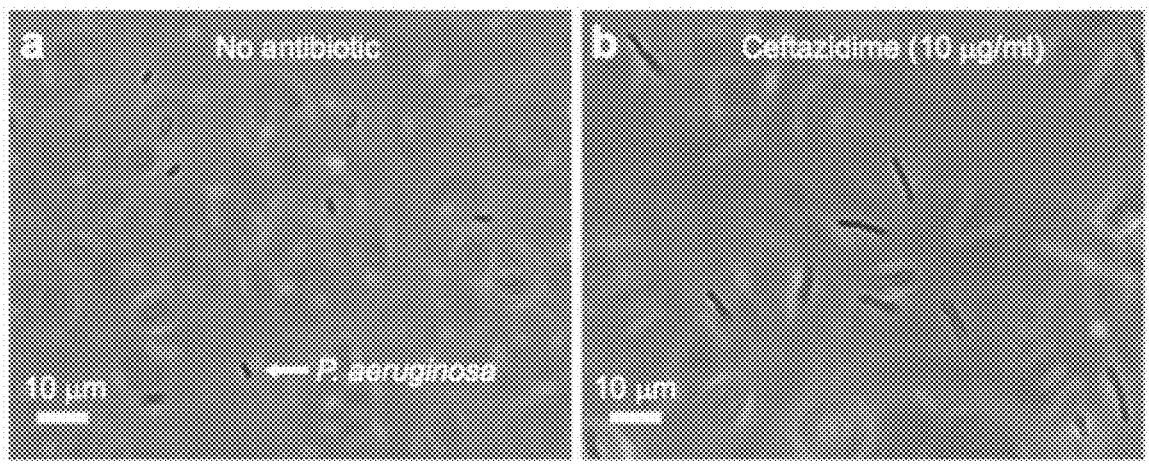

In both of the above cases, when multiple antibiotic conditions are assayed, the software computes the minimum inhibitory concentration (MIC) of the antibiotic for that bacterium (FIG. 19). The software or the user then determines whether this MIC determined from motility lies within the quality control ranges available from literature or directly compares the MIC determined from motility with the MIC of that bacterium determined from parallel testing with gold-standard assays, such as the broth microdilution test. The MIC also yields the diagnostic performance, including the category agreement (susceptible/intermediate/ resistant) and discrepancy rates (major, minor, and very major discrepancies) of a bacterium based on clinical breakpoints published by the Clinical & Laboratory Standards Institute (CLSI) or the European Committee on Antimicrobial Susceptibility Testing (EUCAST).

Figure 5:
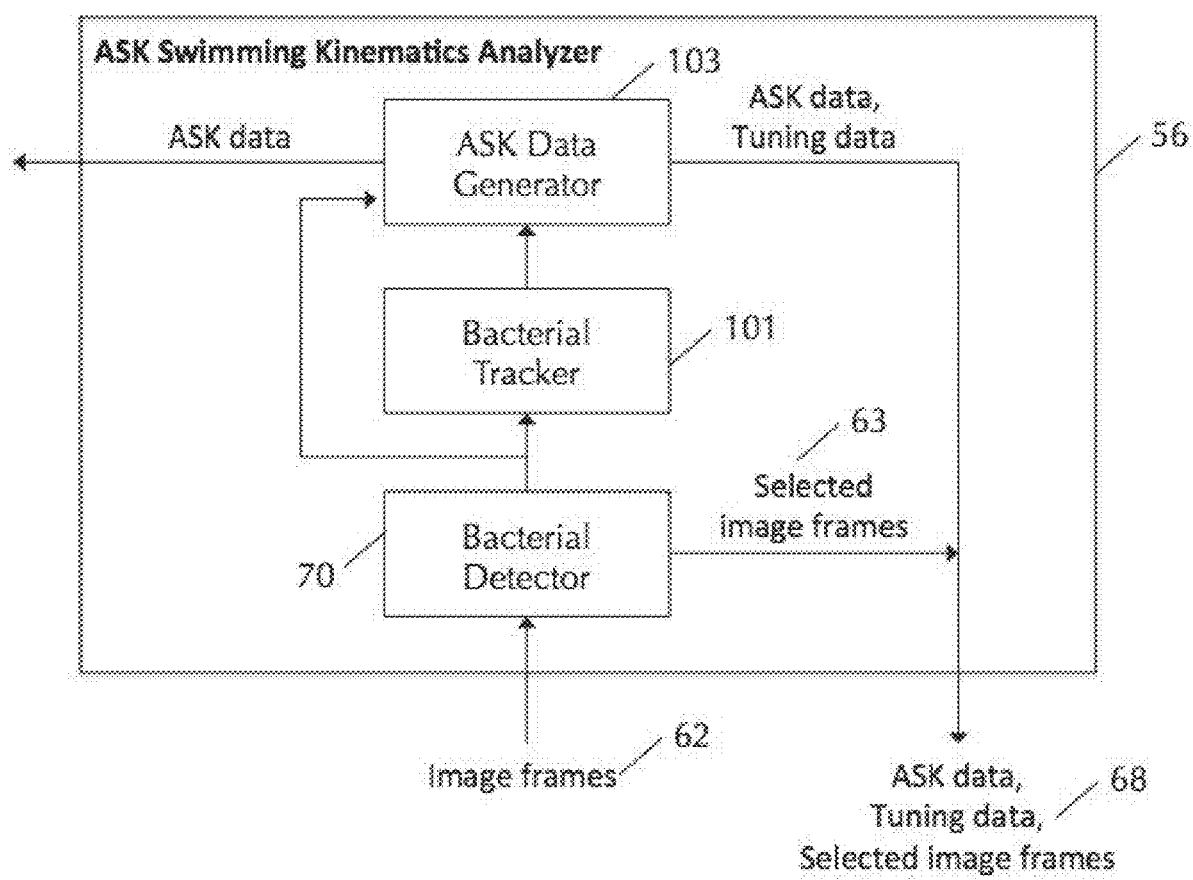

While motility is a very fast phenotype to assay, single-microorganism-level imaging also provides information on other important phenotypes, including number of cells, size of cells, shape of cells, and whether they are in the process of dividing. As shown in FIGS. 5 and 8, these additional phenotypes are available from the detected bacterial data obtained from the bacterial identifier, without the need for further processing through the bacterial tracker. Shape for example can be used to differentiate cocci, bacilli and Vibrios. Size can be used if imaging occurs at short intervals in each well (e.g., 5 to 15 min) to assess growth. Numbers of cells can equally be used to assess growth. In some implementations, the ASK software makes use of motility information together with changes in any one of these other key phenotypes by using a combination of criteria to further enhance the reliability of AST. The combination of phenotype changes can be evaluated in a statistical model that compares the antibiotic treatment results with the antibiotic-free control results.

The swimming kinematics analyzer generates two data sets (FIG. 8): (i) the ASK data 68, and (ii) the tuning data 68. The ASK data includes all quantified swimming kinematics information or detected bacterial data or both. The tuning data includes all the criteria used for microorganism ID or AST or both in the current analysis. The swimming kinematics analyzer sends the tuning data obtained from the current analysis and stores them in the ASK database management system (FIG. 4). Prior data (i.e., historical data) stored in the database is utilized by the ASK tuner module to continuously upgrade the swimming kinematics analyzer and enhance the accuracy of ID or AST (or both) routines in subsequent tests.

Other implementations are also within the scope of the following claims.

For example, although we have discussed antibiotics and their impact on motility of bacteria, the motility techniques that we describe would also apply to any microorganism and to any chemical—antibiotic or otherwise—that is intended to have an effect on the microorganism that is reflected in a change in its motility.

Also, the scope of this method can be expanded to conditions in which the microorganism in a sample is not moving, but has the capability of being motile, or displays reduced motility, for example through the addition of chemical agents (including for example specific nutrients or EDTA) that stimulate motility. In these implementations, the user would first add motility stimulants and then apply the ID and AST techniques or others described above. This approach can also be iterative, e.g., it can be applied, for example, after a pre-screening step in which first the sample has been imaged and no motile bacteria have been detected, in order to enhance the confidence in the absence of motile pathogenic bacteria or to detect those.

EXAMPLES

Here we describe selected examples of swimming kinematics of bacteria, computed from their individual trajectories.

Figure 11:
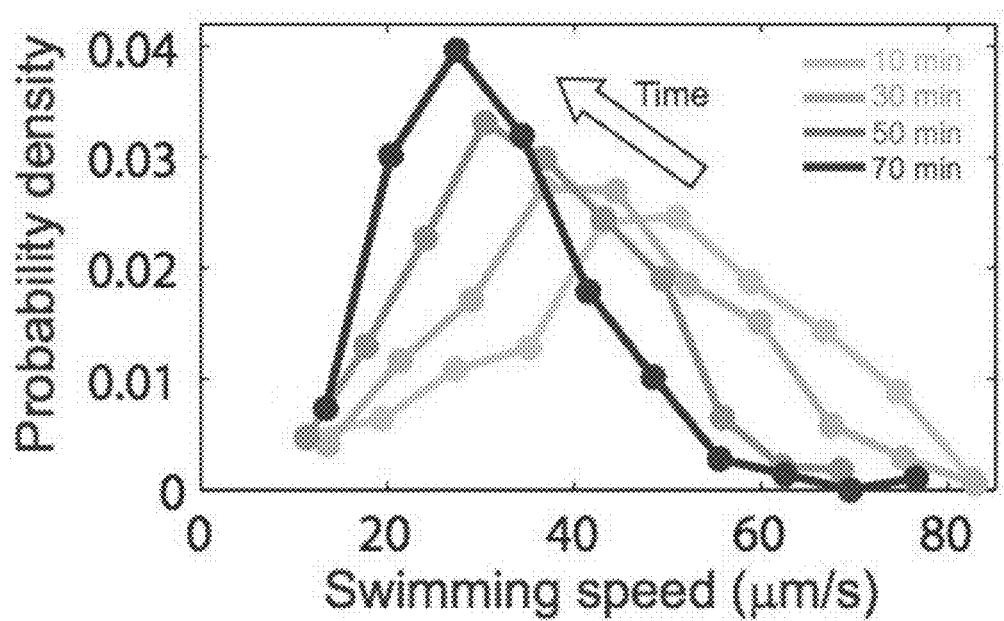
Figure 12:
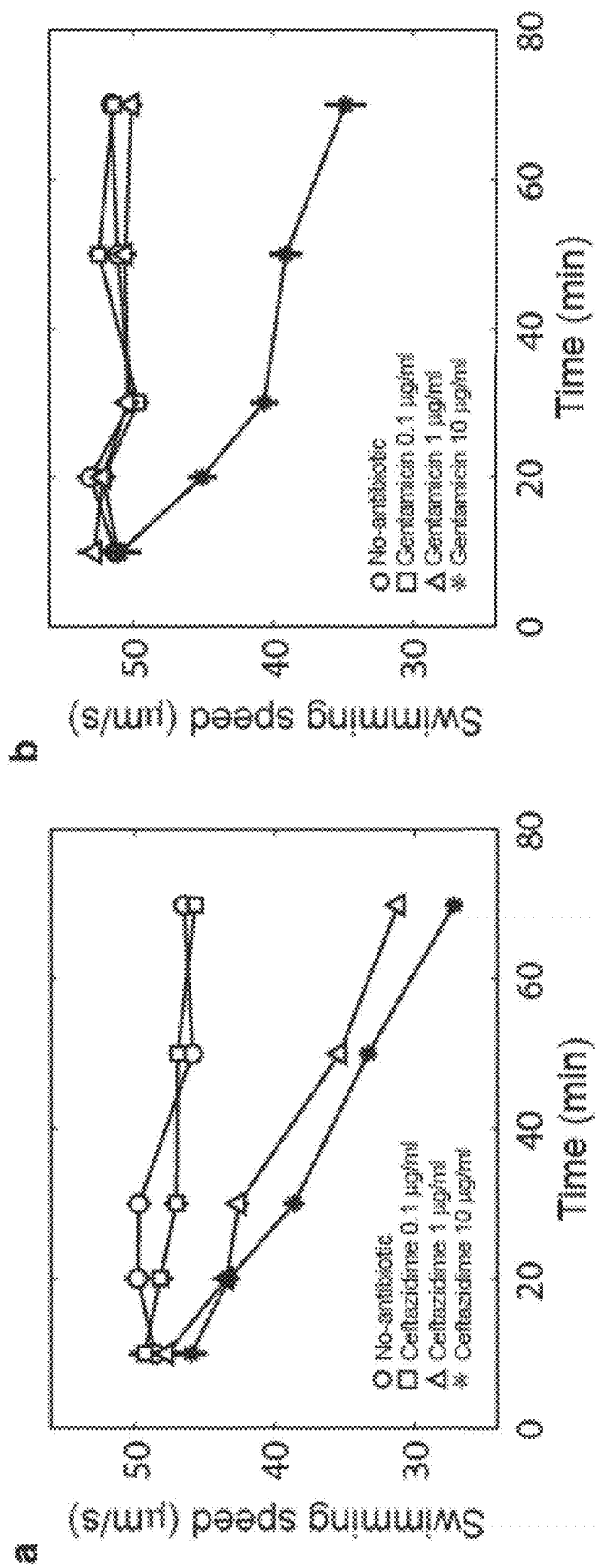

Unpublished experimental data obtained using a highly virulent clinical reference strain, *P. aeruginosa* PA14, demonstrate that exposure to antibiotics changes the pathogen's single-cell-level swimming kinematics, indicating that motility of individual microorganisms is an excellent candidate as a rapid diagnostic biomarker to determine antibiotic susceptibility. For ceftazidime, a β-lactam antibiotic, we observed a decrease in the average swimming speed when *P. aeruginosa* PA14 cells were exposed to the antibiotic (FIGS. 11 and 12). FIG. 11 presents data demonstrating a decrease in the swimming speed of *P. aeruginosa* PA14 over time after exposure to ceftazidime (1 µg/ml) at time zero. The probability density in FIG. 11 denotes the distribution of speeds across individual cells (where at least 257 bacterial trajectories per time point were imaged and analyzed). Specifically, when *P. aeruginosa* PA14 cells were exposed to the β-lactam antibiotic ceftazidime at a concentration of 1 µg/ml (FIGS. 11 and 12) the mean swimming speed of the cells decreased by 14% (49.7 µm/s→42.6 µm/s) after 30 min, by 23% (45.9 µm/s→35.4 µm/s) after 50 min, and by 33% (46.5 µm/s→31.2 µm/s) after 70 min, compared to the antibiotic-free control at the same time points. Importantly, the Analysis of Swimming Kinematics (ASK) software detected the changes in swimming kinematics over a time smaller than the cell division time (see time point at 20 min in FIG. 12), implying that motility can be a biomarker that is much faster to detect than growth. Similar changes in swimming speed were observed upon exposure to 10 µg/ml ceftazidime (FIG. 12), whereas no significant changes in the swimming speed compared to the antibiotic-free control were measured at 0.1 µg/ml ceftazidime (FIG. 12). In FIG. 12, vertical error bars denote standard errors: where not visible, vertical error bars are smaller than symbols.

The ASK software also provided rapid AST results within one cell division when *P. aeruginosa* cells were exposed to gentamicin, a non-β-lactam antibiotic. The pathogens' swimming speed was significantly reduced by exposure to 10 µg/ml gentamicin (FIG. 12) but not to 1 and 0.1 µg/ml gentamicin. For the examples shown here, swimming bacteria were imaged at mid-depth of a well at 30 frames per second by phase contrast microscopy (20× objective) using a digital camera. All analyses were performed using the ASK software (implemented in C++) to identify cells, reconstruct their trajectories, and quantify their swimming kinematics.

Figure 13:
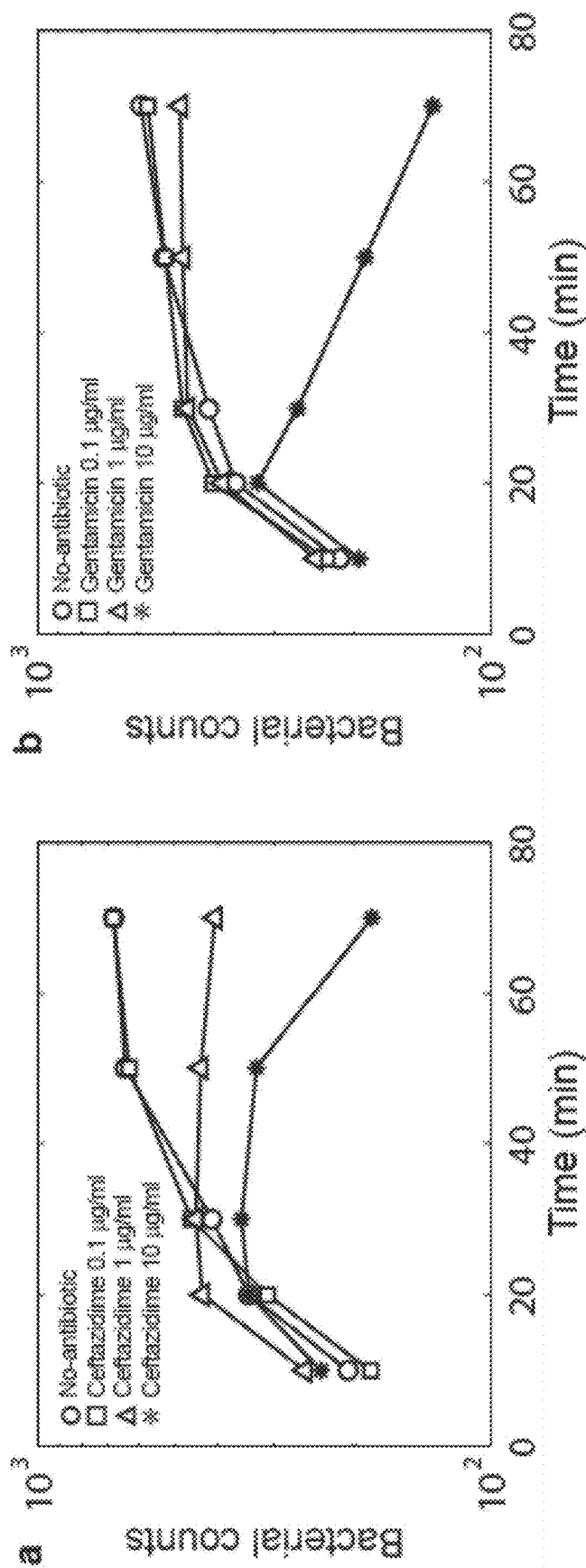

The ASK software can use one or more criteria for rapid AST, as shown here for ceftazidime and gentamicin (FIG. 13). For example, the number of bacteria in a sample over time (FIG. 13) can be used in conjunction with the swimming kinematics data (FIG. 12) to increase the accuracy of AST. FIG. 13 shows the bacteria counts and demonstrates changes in the number of *P. aeruginosa* PA14 cells over time upon exposure to the β-lactam antibiotic ceftazidime (FIG. 12a) and the non-β-lactam antibiotic gentamicin (FIG. 12b), at time zero, with each of the two antibiotics tested at selected concentrations given in the legend of that figure.

Figure 14:
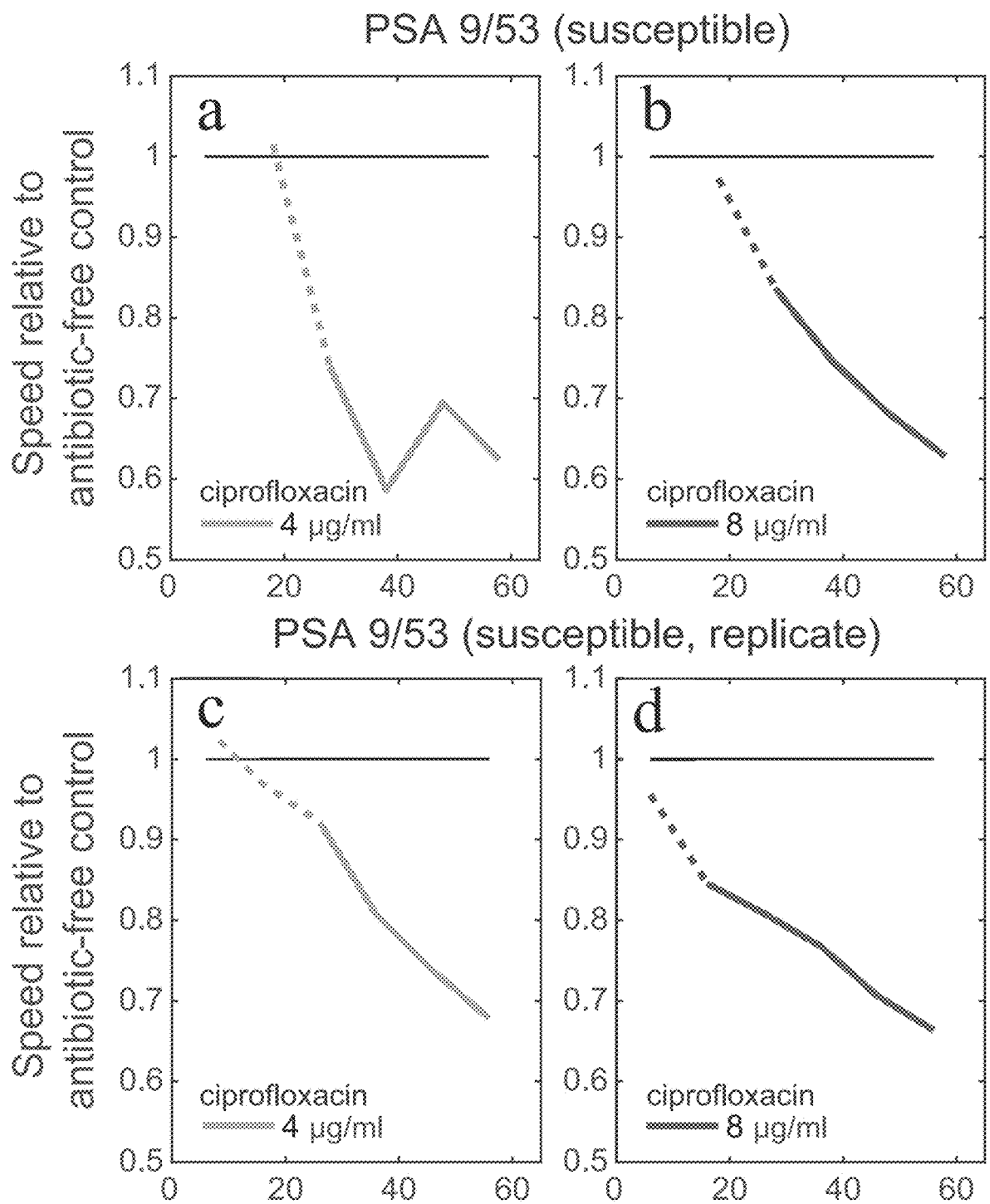
Figure 15:
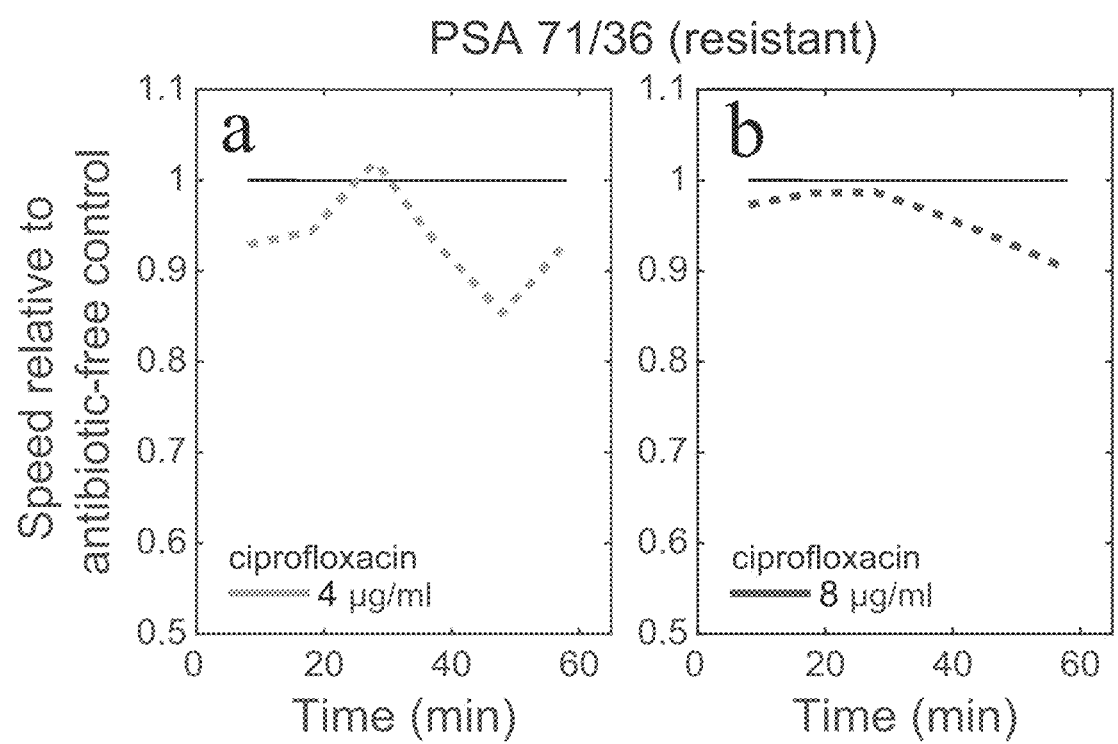
Figure 16:
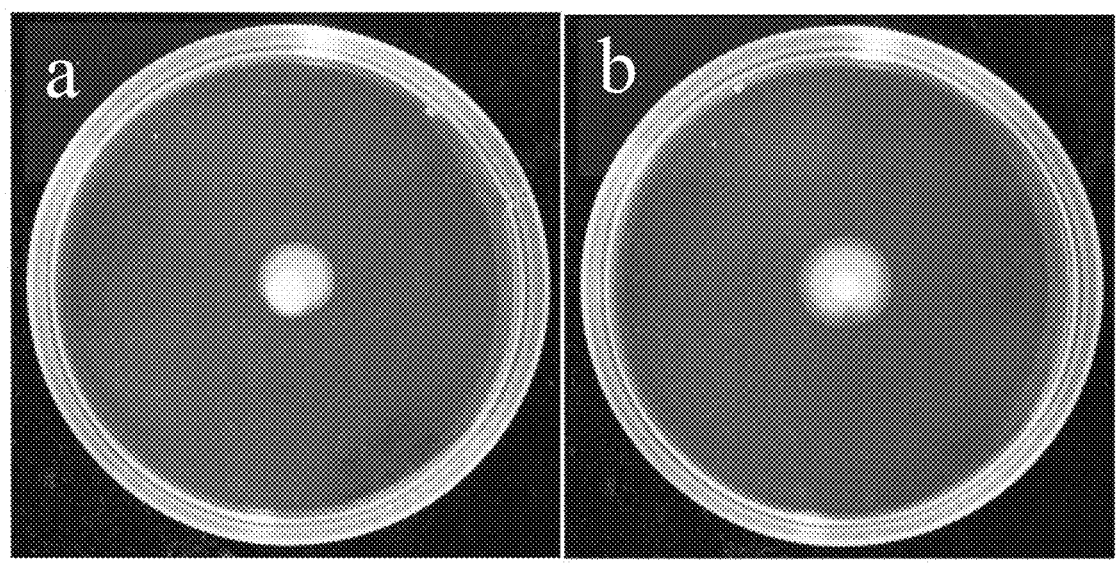

As shown in FIGS. 14 and 15, the ASK software can discriminate, for a given antibiotic, susceptible strains and resistant strains, as shown here with *P. aeruginosa* exposed to ciprofloxacin (FIGS. 14 and 15). FIG. 14 shows that ciprofloxacin impairs motility of a susceptible clinical isolate of *P. aeruginosa* (PSA 9/53, MIC<0.125 µg/ml) and FIG. 15 shows that ciprofloxacin does not impair the motility of a resistant clinical isolate of *P. aeruginosa* (PSA 71/36, MIC=8 µg/ml). In FIG. 14a and FIG. 14c, two replicate experiments for PSA 9/53 for 4 µg/ml ciprofloxacin normalized to the antibiotic-free control (straight line at a value of 1) are shown (CLSI resistant breakpoint: ≥4 µg/ml). The swimming speed (y axis) was normalized by the speed in the control (which thus becomes the dashed line at 1). Antibiotic treatments are displayed as solid lines when the reduction in speed with respect to the control becomes statistically significant (p=0.001), and as dotted lines when there is no statistically significant difference. In FIG. 14b and FIG. 14d, two replicate experiments for PSA 9/53 for 8 µg/ml ciprofloxacin normalized to the antibiotic-free control (straight line at a value of 1) are shown. FIG. 15a and FIG. 15b, experiments for the resistant strain *P. aeruginosa* 71/36 exposed to 4 and for 8 µg/ml ciprofloxacin, normalized to the antibiotic-free control (straight line at a value of 1), are shown. Note how for this resistant strain the speed is never significantly different from the control (lines are always dotted). FIG. 16 show a motility-plate assays for PSA 71/36 assessed after overnight incubation, for the antibiotic-free control (FIG. 16a) and 4 µg/ml ciprofloxacin (FIG. 16b). Note the outward expansion in both cases, denoting no impairment of motility by ciprofloxacin for this resistant strain, as obtained with the ASK software in less than 30 min (FIG. 15a).

Figure 17:
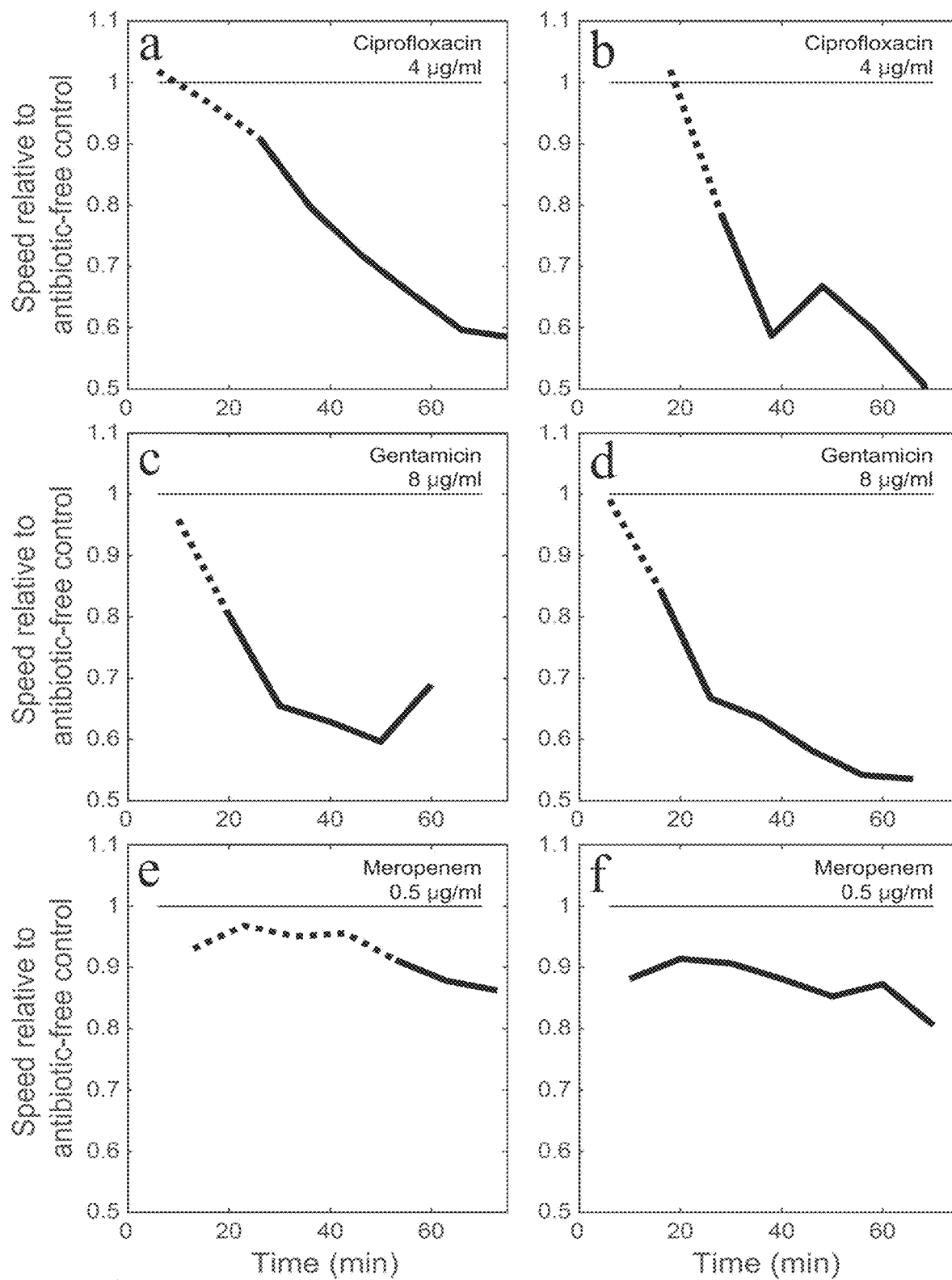
Figure 18:
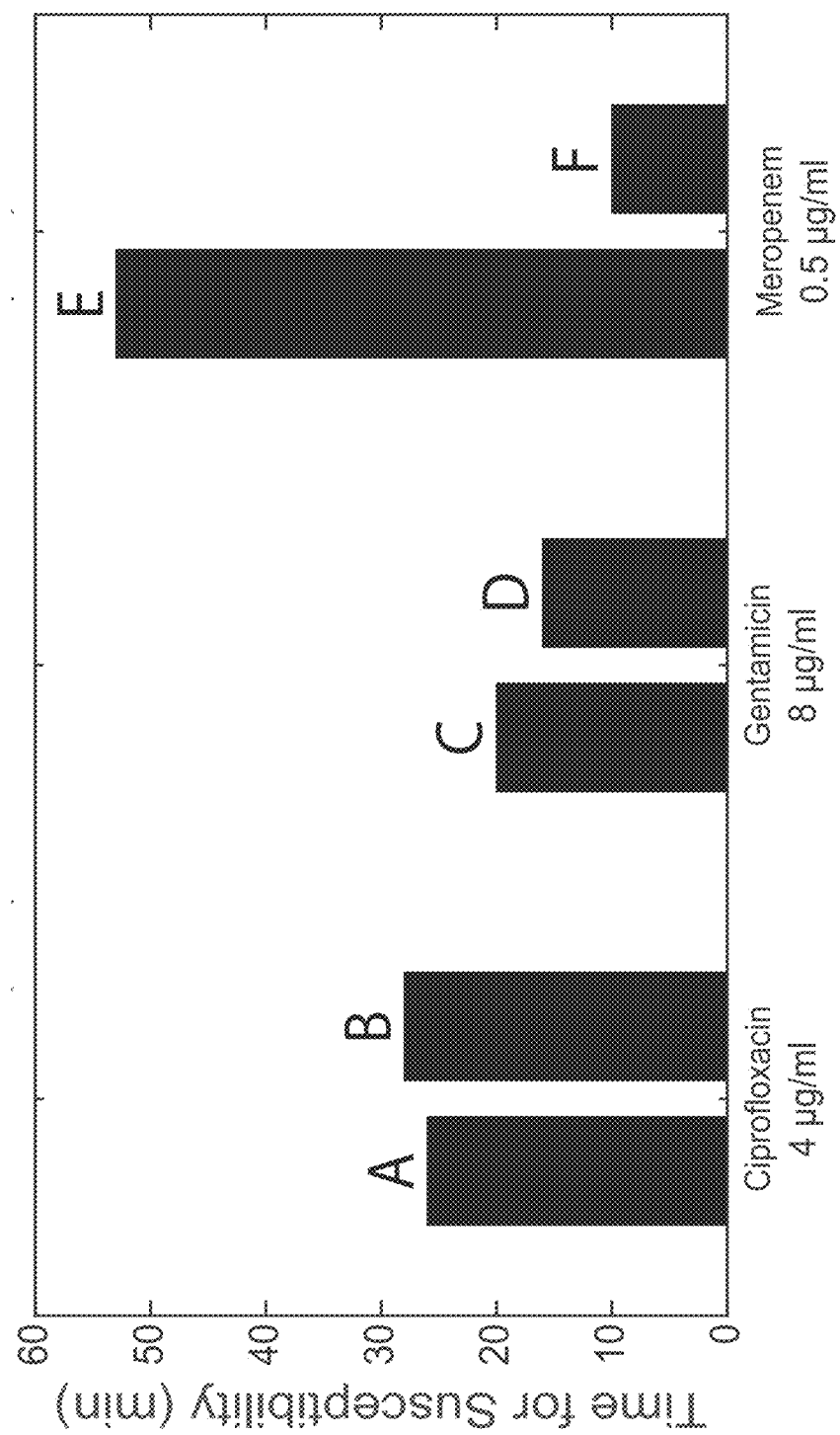

The ASK software provides result on susceptibility of a microorganism to an antibiotic in under an hour, often within 30 minutes (FIG. 17), and potentially even more quickly. FIG. 17 shows the swimming speed of clinical isolate *P. aeruginosa* 9/53 exposed to ciprofloxacin at 4 µg/ml (FIG. 17a and FIG. 17b, showing two replicate experiments), to meropenem at 0.5 µg/ml (FIG. 17c and FIG. 17d, showing two replicate experiments) and to gentamicin at 8 µg/ml (FIG. 17e and FIG. 17f, showing two replicate experiments). Each of FIGS. 17a through 17f shows the swimming speed (relative to speed in the antibiotic-free control case) as a function of time, where lines become solid when speed is significantly lower than in the control (p=0.001). FIG. 18 shows, for all six cases shown in FIGS. 17a through 17f, the time at which susceptibility is first detected (the time at which lines become solid in FIG. 17a through 17f). Note how susceptibility is typically detected in 10-50 min. Note how motility is very sensitive to ciprofloxacin and to gentamicin, less so to meropenem, which shows higher variability yet still provides a statistically significant result. The MIC (determined by broth microdilution assay) was <0.125 µg/ml. (for ciprofloxacin), 0.5 µg/ml (for meropenem) and 1 µg/ml (for gentamicin).

As shown in FIG. 19, changes in swimming speed determined with the ASK software can be used to quantify the MIC of an antibiotic. FIG. 19 shows the swimming speed (relative to the antibiotic-free control case) as a function of time, for the reference strain *P. aeruginosa* ATCC 27853 exposed to different concentrations of gentamicin (MIC 1 µg/ml, as determined by broth microdilution assay). Lines become solid when speed is significantly lower than control (p=0.001). Note how the 1 µg/ml curve reveals susceptibility after 35 min of exposure.

REFERENCES

A widely used AST method in clinical microbiology laboratories relies on manual or automated measurements of bacterial growth upon antibiotic exposure (1, 2); all numerical citations are to the references set forth below). Manual methods, including the disk-diffusion test and the Etest gradient-diffusion tests, are simple and standardized (1, 2) and provide both qualitative information (categorizing bacteria as susceptible, intermediate, or resistant) and quantitative information (minimum inhibitory concentration, MIC). Automated systems are based on broth dilution tests (reviewed in (3)), detect subtle changes in growth through sensitive optical systems, and provide the same information as manual tests. Multiple automated systems cleared by the FDA for use in the United States exist (2), including the MicroScan WalkAway (Siemens Healthcare Diagnostics), the BD Phoenix Automated Microbiology System (BD Diagnostics) and the Vitek 2 System (bioMerieux). These conventional methods rely on bacterial growth and on the sample reaching a sufficiently high bacterial concentration for robust detection, which takes from many hours to days.

A number of systems have emerged over the past several years to speed up ID/AST, based on phenotypic traits measured at the single-cell level. These assays are still often based on measurements of growth, sometimes in combination with morphology of cells that are immobilized on a surface (4, 5). The commercial systems include:

- The Accelerate Pheno system (Accelerate Diagnostics) 10 uses single-cell-level imaging to measure morphological changes as a biomarker for AST in an automated manner Fluorescence in-situ hybridization is used for ID in the same system. Average time to results is 90 min for ID and 7 h for AST, starting from a positive blood culture that typically requires an overnight incubation. While it uses single-cell imaging, this approach is limited to measuring changes in morphology and is only applicable to cells immobilized on a 15 surface.
- The QMAC dRAST system (Quanta Matrix) uses microfluidic technology and single-cell imaging to measure morphological changes as a biomarker for AST (4). Average time to result for AST is 4 h from a positive blood culture that typically requires an overnight incubation. This approach is applicable to cells that are immobilized (embedded in a 20 gel) and requires a priori information on pathogen ID.
- The LifeScale AST system (LifeScale) uses microfluidic technology to detect changes in cell numbers and single-cell mass as biomarkers for AST. Video microscopy further yields single-cell morphology information. Time to result for AST is approximately 3 to 4 hours from a positive blood culture that typically requires an 25 overnight incubation. This approach requires a priori information on pathogen ID.
- The 216Dx UTI system (Bacterioscan) uses laser-scattering technology to measure the growth of bacteria in a suspension in order to screen urine specimens as positive or negative, with a 3 h turnaround time. Another system (216R AST), advertised as being in the making, is projected to extend the same technology to AST, but is still under 30 development.
- The oCelloScope system (BioSense Solutions) uses time-lapse imaging of cells attached to the surfaces of wells in a 96-well plate for fast growth measurements. Changes in growth can be used as biomarker for AST.
- The mariPOC and mariAST systems (Arcdia) provide ID based on bacterial growth, measured with an immunoassay binding reaction on latex microbeads and detected using two-photon excitation fluorometry. This system yields ID in 20 min and AST in 2 h for a positive inoculum that is obtained after at least an overnight incubation.
- The fASTest system (6) uses a known microfluidic chip design called the Mother Machine (7) to measure single-cell growth rates in the presence of antibiotics using microscopy. Time to result for AST can be less than 30 min using a bacterial culture with pure isolates. In this approach, bacteria are trapped within highly confined microchannels. This approach requires a priori information on pathogen ID.
- The rapid dLAMP system (8) uses digital loop-mediated isothermal amplification (dLAMP) to measure the antibiotic susceptibility of E. coli within clinical urine samples. The study refers to the method as 'phenotypic', but the assessment is based on digital nucleic acid quantification. Time to result for AST is less than 30 minutes from clinical urine samples.

Other commercial phenotypic approaches exist.

Other systems have been proposed to accelerate AST based on genotypic approaches, which enable detection of resistance genes. A large number of other genotypic approaches exist.

Other long-known and used approaches to test the viability of spermatozoa are based on morphology, counts, and motility. One example is Green (US patent publication 2007/0298454). King et al. (*Antibiotics: effect on cryopreserved-thawed human sperm motility in vitro*, Fertility and Sterility, 1997, vol. 67, no. 6, pp. 1146-1151), used a commercial system to analyze motility of spermatozoa incubated over a 48-hour period in the presence of antibiotics to assess their fertilizing capacity.

In addition, a body of literature addresses the effects of antibiotics on motility. The majority of these are population-level studies, which have demonstrated effects of several antibiotics on several bacterial species (9-11). These approaches are often based on the classic disk-diffusion motility assay and have limited discriminatory power (only outward movement of the population is measured; FIG. 16). A small number of studies have used single-cell approaches to study motility in the presence of antibiotics, and have mainly focused on ecological significance of antibiotic exposure. Cheong et al. (12) imaged single-cell motility using holographic microscopy and presented a single proof-of-concept experiment, exposing *E. coli* to a very high concentration of gentamicin (15 mg/mL; a concentration that is more than 4000-fold higher than the susceptible breakpoint concentration from the CLSI). In an ecological study, Graff et al. (13) exposed *Vibrio cholerae* to a gradient of the antibiotic produced by a competitor bacterium in the ocean (andrimid) and used single-cell imaging to show an avoidance response of high antibiotic concentrations. They quantified selected swimming kinematics. Comparison of different antibiotic concentrations was performed along an antibiotic gradient. Hol et al. (14) used single-cell imaging of *E. coli* to show that when bacteria are in very high concentrations ($>5\times10^9$ cells/ml; for example, in the gold standard broth microdilution assay used for AST the initial inoculum concentration is typically $5\times10^5$ CFU/ml; CFU=colony forming units) the bacteria can colonize an antibiotic (kanamycin) landscape. These authors demonstrated that bacteria in these high concentrations swim towards higher concentrations of the antibiotic.

1. Clinical Laboratory Standard Institute, Performance Standards for Antimicrobial Susceptibility Testing; Twenty-Fifth Informational Supplement (2015).
2. J. H. Jorgensen, M. J. Ferraro, Antimicrobial Susceptibility Testing: A review of general principles and contemporary practices. *Clin Infect Dis* 49, 1749 (2009).
3. I. Wiegand, K. Hilpert, R. E. W. Hancock, Agar and broth dilution methods to determine the minimal inhibitory concentration (MIC) of antimicrobial substances. *Nat Protoc* 3, 163 (2008).
4. J. Choi et al., A rapid antimicrobial susceptibility test based on single-cell morphological analysis. *Sci Transl Med* 6, 267 (2014).
5. Y. Matsumoto et al., A microfluidic channel method for rapid drug-susceptibility testing of *Pseudomonas aeruginosa*. *PLoS ONE* 11, e0143797 (2016).

6. O. Baltekin, A. Boucharin, E. Tano, D. I. Andersson, J. Elf, Antibiotic susceptibility testing in less than 30 min using direct single-cell imaging. *Proc Natl Acad Sci USA* 114, 9170 (2017).
7. P. Wang et al., Robust growth of *Escherichia coli*. *Curr Biol* 20, 1099-1103 (2010).
8. N. G. Schoepp, T. S. Schlappi, M. S. Curtis, S. S. Butkovich, S. Miller, R. M. Humphries, R. F. Ismagilov, Rapid pathogen-specific phenotypic antibiotic susceptibility testing using digital LAMP quantification in clinical samples. *Sci Transl Med* 9, 410 (2017).
9. L. R. Hoffman et al., Aminoglycoside antibiotics induce bacterial biofilm formation. *Nature* 436, 1171 (2005).
10. J. F. Linares, I. Gustafsson, F. Baquero, J. L. Martinez, Antibiotics as intermicrobial signaling agents instead of weapons. *Proc Natl Acad Sci USA* 103, 19484 (2006).
11. A. P. Fonseca, J. C. Sousa, Effect of antibiotic-induced morphological changes on surface properties, motility and adhesion of nosocomial *Pseudomonas aeruginosa* strains under different physiological states. *J Appl Microbiol* 103, 1828 (2007).
12. F. C. Cheong et al., Rapid, high-throughput tracking of bacterial motility in 3D via phase-contrast holographic video microscopy. *Biophys J* 108, 1248 (2015).
13. J. R. Graff, S. R. Forschner-Dancause, S. Menden-Deuer, R. A. Long, D. C. Rowley, *Vibrio cholerae* exploits sub-lethal concentrations of a competitor-produced antibiotic to avoid toxic interactions. *Front Microbiol* 4, 8 (2013).
14. F. J. H. Hol, B. Hubert, C. Dekker, J. E. Keymer, Density-dependent adaptive resistance allows swimming bacteria to colonize an antibiotic gradient. *ISME J* 10, 30 (2016).

ADDITIONAL REFERENCES a. R. O. Davis et al., Quantitative analysis of sperm motion kinematics from real-time video-edge image. *Proc. SPIE* 0832, *High Speed Photography, Videography, and Photonics* V, 14, doi:10.1117/12.942202 (1988).
b. R. Green, E. Gillies, R. Cannon and A. Pacey, *Analysis of cell morphology and motility*, US patent publication 2007/0298454.
c. E. Lauga and T. R. Powers, The hydrodynamics of swimming microorganisms, *Rep Prog Phys* 72, 096601 (2009).
d. J. M. Brubacher, Microorganism Evaluation System, US patent publication 2015/0167045.
e. King et al., Antibiotics: effect on cryopreserved-thawed human sperm motility in vitro. *Fertility and Sterility,* 67, 1146 (1997).
f. E. Lauga, Bacterial hydrodynamics, *Annu Rev Fluid Mech* 48, 105 (2016).
g. W. Hu et al., Interplay between type IV pili activity and exopolysaccharides secretion controls motility patterns in single cells of *Myxococcus xanthus*. *Sci Rep,* 6, 17790 (2016).
h. I. G. de Jong, K. Beilharz, O. P. Kuipers and J.-W. Veening, Live cell imaging of *Bacillus subtilis* and *Streptococcus pneumoniae* using automated time-lapse microscopy, *J Vis Exp,* 53, 3145 (2011).
i. K. Ritchie et al., Single-molecule imaging in live bacteria cells, *Philos Trans R Soc Lond B Biol Sci.* 368, 20120355 (2013).
j. T. Emonet et al., AgentCell: A digital single-cell assay for bacterial chemotaxis. *Bioinformatics* 21, 2714 (2005).

Other implementations are also within the scope of the following claims.

The invention claimed is:

1. A method comprising:
    (a) subjecting a first portion and a second portion of a bodily sample of a human or an animal to different known concentrations of one or more antibiotics, the first portion and the second portion each containing one or more individual bacteria or fungi of one or more strains;
    (b) by an imaging device, capturing one or more images of the first portion and one or more images of the second portion;
    (c) by computer, measuring physical trajectories of the one or more individual bacteria or fungi from the one or more captured images of the sample first portion;
    (d) by computer, generating motility kinematics data corresponding to the measured physical trajectories for at least one of the one or more individual bacteria or fungi of one or more strains in the first portion;
    (e) by computer, measuring physical trajectories from the one or more captured images of the second portion;
    (f) by computer, generating motility kinematics data corresponding to the measured physical trajectories for at least one of the one or more individual bacteria or fungi of one or more strains in the second portion;
    (g) by computer, determining from the motility kinematics data a first physical motility of the at least one of the one or more individual bacteria or fungi of one or more strains in the first portion and a second first physical motility of the at least of the one or more individual bacteria or fungi of one or more strains in the second portion;
    (h) by computer, comparing the first determined physical motility and the second determined physical motility and generating a magnitude of a difference between the first determined physical motility and the second determined physical motility; and
    (i) by computer, identifying one or more strains of bacteria or fungi from the magnitude of the difference between the first determined physical motility and the second determined physical motility and from stored data indicative of relationships of physical motility of bacteria or fungi to identify one or more strains of bacteria or fungi subjected to the one or more known concentrations of antibiotics.

2. The method of claim 1 in which the generating of the motility kinematics data comprises generating mean square displacement data for the one or more individual bacteria or fungi of one or more strains.

3. The method of claim 1 in which the determining of the identity of one or more strains of bacteria or fungi is based on a feature of the motility kinematics data of the one or more individual bacteria or fungi of one or more strains other than the generated mean square displacement data.

4. The method of claim 3 in which the feature of the motility kinematics data other than the generated mean square displacement data is based on one or a combination of two or more of the following kinematics of the one or more individual bacteria or fungi of one or more strains: speed, acceleration, turning rate, angle of turning, movement pattern, shape of trajectory, diffusivity, net-two-gross-displacement-ratio, trajectory curvature, wobble, and change in fraction of motile bacteria or fungi relative to non-motile bacteria or fungi.

5. The method of claim 1 in which the identifying one or more strains of bacteria or fungi is based on a characteristic other than the generated kinematics data.

6. The method of claim 5 in which the characteristic comprises a morphological feature or a spatial arrangement of the one or more individual bacteria or fungi of one or more strains.

7. The method of claim 6 in which the morphological feature comprises one or a combination of two or more of the following: shape, aspect ratio, convexity, area, size, dimension, direction of major axis, departure from spherical shape, or distribution of intensity, and the spatial arrangement comprises one or a combination of two or more of the following: a spatial arrangement of one or more individual bacteria or fungi that are dividing, a spatial arrangement of a cluster of individual bacteria or fungi , positions of two or more bacteria or fungi relative to each other, one or more distances between them, or a formation of specific clusters or chains of the individual bacteria or fungi.

8. The method of claim 1 in which the measuring physical trajectories comprises processing the one or more captured images, the processing including (a) locating bacteria or fungi based on at least one of color, pixel intensity gradient, shape, aspect ratio, convexity, area, size threshold, horizontal and vertical location, size, intensity, direction of major axis, departure from spherical shape, or distribution of intensity, and (b) constructing physical trajectories dat by linking the same bacteria or fungi located in two or more of the images based on at least one of position, proximity of position, direction, velocity, acceleration, or search radius.

9. The method of claim 1 comprising determining the presence, absence, or count of moving microorganisms in a pre-screening step.

10. The method of claim 1 comprising changing at least one environmental condition to stimulate movement of the one or more individual bacteria or fungi.

11. The method of claim 1 comprising removing non-moving microorganisms from the images by image analysis or physically from the sample.

12. The method of claim 1 in which the bodily sample comprises one or more isolates that have been cultured from the sample.

13. The method of claim 1 in which the sample comprises one or a combination of two or more of an anticoagulant, a clot activator, a gel-barrier, a growth stabilizer, an antiglycolytic agent, a solid, debris, a non-fluid sample material, ground food, food particles, an environmental sample, a preservative, an inhibitor, a medium, or an additive or another fluid, in addition to the one or more antibiotics.

14. The method of claim 1 comprising determining an antibiotic of choice to treat an infection or other disease caused by the one or more individual bacteria or fungi.

15. The method of claim 1 in which the one or more strains of bacteria identified is selected from the group consisting of *Escherichia coli, Pseudomonas aeruginosa, Vibrio cholerae* and other *Vibrio* strains, *Helicobacter pylori, Campylobacter jejuni, Salmonella typhimurium, Listeria monocytogenes, Acinetobacter baumannii, Borrelia burgdorferi* and other *Borrelia* strains, some *Bacillus* strains, *Bartonella* strains, *Clostridium* strains, *Legionella* strains, *Leptospira* strains, *Neisseria* strains, *Mycoplasma*, and *Treponema*.

16. The method of claim 1 in which one of the different known concentrations comprises a zero concentration.

17. A method comprising:
(a) subjecting a first portion and a second portion of a bodily sample of a human or an animal to different known concentrations of one or more antibiotics, the first portion and the second portion each containing one or more individual bacteria or fungi of one or more strains having a movement in the sample, the movement resulting from an external influence other than the one or more antibiotics;
(b) by an imaging device, capturing in at least two different contexts one or more images of the first portion and one or more images of the second portion;
(c) by computer, measuring physical trajectories from the one or more captured images of the first portion corresponding to the movement of the one or more individual bacteria or fungi of one or more strains resulting from the external influence;
(d) by computer, generating motility kinematics data corresponding to the measured physical trajectories for at least one of the one or more individual bacteria or fungi of one or more strains in the first portion;
(e) by computer, measuring physical trajectories from the one or more captured images of the second portion corresponding to the movement of the one or more individual bacteria or fungi of one or more strains resulting from the external influence;
(f) by computer, generating motility kinematics data corresponding to the measured physical trajectories for at least one of the one or more individual bacteria or fungi of one or more strains in the second portion;
(g) by computer, determining from the motility kinematics data a first physical motility of the at least one of the one or more individual bacteria or fungi of one or more strains in the first portion and a second first physical motility of the at least of the one or more individual bacteria or fungi of one or more strains in the second portion;
(h) by computer, comparing the first determined physical motility and the second determined physical motility and generating a magnitude of a difference between the first determined physical motility and the second determined physical motility; and
(i) by computer, identifying one or more strains of bacteria or fungi from the magnitude of the difference between the first determined physical motility and the second determined physical motility and from stored data indicative of relationships of physical motility of bacteria or fungi to identify one or more strains of bacteria or fungi subjected to the one or more known concentrations of antibiotics.

18. The method of claim 17 in which the external influence is associated with Brownian motion of the one or more individual bacteria or fungi.

19. The method of claim 17 in which the two different contexts comprise two different times at which the one or more images of the sample are captured.

20. The method of claim 17 in which one of the different known concentrations comprises a zero concentration.

21. The method of claim 17 in which the sample comprises a sample taken directly from the human or the animal or one or more isolates cultured from the sample.

22. The method of claim 17 in which the movement comprises movement at, near, towards or otherwise with respect to a surface of the sample.

23. The method of claim 17 in which the movement in the sample results from motility.

24. The method of claim 23 in which the motility comprises motility effected by flagella, pili, fimbriae, or other appendages or propulsion mechanisms, or combinations of such motilities.

25. The method of claim 23 in which the motility comprises at least one of swimming, twitching, gliding, swarming, or another form of motility exhibited by microorganisms.

* * * * *